United States Patent
Rubin

(10) Patent No.: US 10,984,152 B2
(45) Date of Patent: Apr. 20, 2021

(54) SIMULATING QUANTUM SYSTEMS WITH QUANTUM COMPUTATION

(71) Applicant: Rigetti & Co., Inc., Berkeley, CA (US)

(72) Inventor: Nicholas Charles Rubin, Berkeley, CA (US)

(73) Assignee: Rigetti & Co, Inc., Berkeley, CA (US)

( * ) Notice: Subject to any disclaimer, the term of this patent is extended or adjusted under 35 U.S.C. 154(b) by 428 days.

(21) Appl. No.: 15/720,088

(22) Filed: Sep. 29, 2017

(65) Prior Publication Data

US 2018/0096085 A1 Apr. 5, 2018

Related U.S. Application Data

(60) Provisional application No. 62/402,278, filed on Sep. 30, 2016.

(51) Int. Cl.
*G06N 10/00* (2019.01)
*G06F 30/20* (2020.01)
*G06F 9/455* (2018.01)

(52) U.S. Cl.
CPC .............. *G06F 30/20* (2020.01); *G06F 9/455* (2013.01); *G06N 10/00* (2019.01)

(58) Field of Classification Search
USPC .................. 703/2, 22, 19; 708/200; 702/186
See application file for complete search history.

(56) References Cited

U.S. PATENT DOCUMENTS

| | | | |
|---|---|---|---|
| 7,875,876 B1 | 1/2011 | Wandzura et al. | |
| 8,175,995 B2 | 5/2012 | Amin | |
| 8,832,164 B2 * | 9/2014 | Allen | G06N 10/00 708/200 |
| 8,832,165 B2 * | 9/2014 | Allen | G06N 10/00 708/200 |
| 9,286,154 B2 * | 3/2016 | Ashikhmin | G06N 10/00 |

(Continued)

FOREIGN PATENT DOCUMENTS

| | | |
|---|---|---|
| CN | 105787292 | 7/2016 |
| WO | 2005/122052 | 12/2005 |
| WO | 2013/006836 | 1/2013 |

OTHER PUBLICATIONS

Advanced Micro Devices, Inc; "What is Heterogeneous Computing", AMD Developer Central; http://developer.amd.com/resources/heterogenous-computing/what-is-heterogeneous-computing/; copyright 2014; accessed Aug. 9, 2015; 7 pgs.

(Continued)

*Primary Examiner* — Thai Q Phan
(74) *Attorney, Agent, or Firm* — Henry Patent Law Firm PLLC

(57) ABSTRACT

In some aspects, a quantum simulation method includes generating a set of models representing a quantum system. The set of models includes subsystem models representing respective fragments of the quantum system. The quantum system is simulated by operating the set of models on a computer system that includes a classical processor unit and multiple unentangled quantum processor units (QPUs), and the unentangled QPUs operate the respective subsystem models. In some examples, density matrix embedding theory (DMET) is used to compute an approximate ground state energy for the quantum system.

34 Claims, 7 Drawing Sheets

(56) References Cited

U.S. PATENT DOCUMENTS

| | | | |
|---|---|---|---|
| 9,819,347 B2* | 11/2017 | Hastings | H03K 19/195 |
| 10,127,499 B1 | 11/2018 | Rigetti et al. | |
| 10,402,743 B1 | 9/2019 | Rigetti et al. | |
| 10,633,248 B2* | 4/2020 | Ashikhmin | G06N 10/00 |
| 10,650,324 B1 | 5/2020 | Rigetti et al. | |
| 10,671,559 B2* | 6/2020 | Mohseni | G06F 15/80 |
| 10,698,789 B1* | 6/2020 | Liu | G06F 11/3664 |
| 2005/0005266 A1 | 1/2005 | Datig | |
| 2005/0182614 A1 | 8/2005 | Meredith | |
| 2005/0273306 A1† | 12/2005 | Hilton et al. | |
| 2006/0101236 A1 | 5/2006 | Han | |
| 2006/0224547 A1* | 10/2006 | Ulyanov | G06N 10/00 706/62 |
| 2009/0070402 A1 | 3/2009 | Rose et al. | |
| 2009/0075825 A1† | 3/2009 | Rose et al. | |
| 2009/0157778 A1* | 6/2009 | Allen | G06N 10/00 708/200 |
| 2009/0164435 A1* | 6/2009 | Routt | B82Y 10/00 |
| 2011/0137632 A1† | 6/2011 | Paxson et al. | |
| 2011/0238378 A1* | 9/2011 | Allen | G06N 10/00 702/186 |
| 2011/0313741 A1* | 12/2011 | Langhoff | G16C 20/30 703/2 |
| 2012/0079177 A1 | 3/2012 | Brewer et al. | |
| 2012/0192200 A1 | 7/2012 | Rao et al. | |
| 2012/0254586 A1 | 10/2012 | Amin et al. | |
| 2013/0160016 A1 | 6/2013 | Gummaraju et al. | |
| 2013/0222399 A1 | 8/2013 | Bourd et al. | |
| 2013/0332702 A1 | 12/2013 | Boudier | |
| 2014/0164313 A1* | 6/2014 | Alboszta | G06N 7/005 706/52 |
| 2014/0297247 A1 | 10/2014 | Troyer et al. | |
| 2014/0354326 A1* | 12/2014 | Bonderson | G06N 10/00 326/5 |
| 2015/0142398 A1† | 5/2015 | Miller, III et al. | |
| 2017/0161632 A1* | 6/2017 | Freedman | B82Y 10/00 |
| 2017/0179960 A1* | 6/2017 | Hastings | G06N 10/00 |

OTHER PUBLICATIONS

Bauer, Bela, et al., "Hybrid quantum-classical approach to correlated materials", 1510.03859v2 [quant-ph], Aug. 29, 2016, 11 pgs.
Booth, et al., "Spectral functions of strongly correlated extended systems via an exact quantum embedding", Physical Review B91, 155107, 2015, 6 pgs.
Bravyi, et al., "Improved Classical Simulation of Quantum Circuits Dominated by Clifford Gates", arXiv:1601.07601v2 [quant-ph], Jan. 27, 2017, 20 pgs.
Bravyi, et al., "Trading classical and quantum computational resources", arXiv:1506.01396v1 [quant-ph], Jun. 3, 2015; 14 pgs.
Bulik, et al., "Can single-reference coupled cluster theory describe static correlation?", arXiv:1505.01894v1 [physics.chem-ph] May 8, 2015, May 11, 2015, 10 pgs.
Bulik, et al., "Density matrix embedding from broken symmetry lattice mean fields", Physical Review B89, 035140, Jan. 27, 2014, 12 pgs.
Bulik, "Electron correlation in extended systems via quantum embedding", Doctoral thesis, Rice University, May 2015, 117.
Bulik, et al., "Electron correlation in solids via density embedding theory", The Journal of Chemical Physics 141, 054113, Aug. 7, 2014, 10 pgs.
Corcoles, et al., "Process verification of two-qubit quantum gates by randomized benchmarking", Physical Review A 87, 030301(R)(2013), Mar. 19, 2013; 4 pgs.
Crawford, et al., "An Introduction to Coupled Cluster Theory for Computational Chemists", Reviews in Computational Chemistry, vol. 14, 2000, 104 pgs.
Dallaire-Demers, Pierre-Luc, et al., "Quantum gates and architecture for the quantum simulation of the Fermi-Hubbard model", arXiv:1606.00208v1 [quant-ph], Jun. 2, 2016, 13 pgs.
Gidofalvi, et al., "Multireference self-consistent-field energies without the many-electron wave function through a variational low-rank two-electron reduced-density-matrix method", The Journal of Chemical Physics 127, 244105, Dec. 28, 2007, 6 pgs.
Helgaker, et al., "Molecular Electronic-Structure Theory", John Wiley & Sons Ltd., West Sussex, England, 2000, 8 pgs.
Hosteny, et al., "Ab initio study of the pi-electron states of trans-butadiene", The Journal of Chemical Physics, vol. 62, No. 12, Jun. 15, 1975, 16 pgs.
Knizia, et al., "Density Matrix Embedding: A Simple Alternative to Dynamical Mean-Field Theory", Physical Review Letters PRL 109,186404, Nov. 2, 2012, 5 pgs.
Knizia, et al., "Density Matrix Embedding: A Strong-Coupling Quantum Embedding Theory", Journal of Chemical Theory and Computation, Feb. 21, 2013, 5 pgs.
Kreula, et al., "Few-qubit quantum-classical simulation of strongly correlated lattice fermions", EPJ Quantum Technology 3:11, 2016, 19 pgs.
Lieb, et al. "The one-dimensional Hubbard model: a reminiscence", Physica A 321; www.elsevier.com/locate/physa, 2003, 27 pgs.
McClean, Jarrod Ryan, "Algorithms Bridging Quantum Computation and Chemistry", Doctoral dissertation, Harvard University, Graduate School of Arts & Sciences; http://nrs.harvard.edu/urn-3:HUL.InstRepos:17467376, May 1, 2015, 245 pgs.
McClean, J. R., et al., "Hybrid Quantum-Classical Hierarchy for Mitigation of Decoherence and Determination of Excited States", arXiv:1603.05681v1 [quant-ph], Mar. 17, 2016, 10 pgs.
McClean, et al., "The theory of variational hybrid quantum-classical algorithms", New J. Phys. 18 (2016)023023, Feb. 5, 2016, 23 pgs.
Neilsen, et al., "Quantum Computation and Quantum Information", Cambridge University Press; Cambridge, UK, 2010, 13 pgs.
O'Malley, et al., "Scalable Quantum Simulation of Molecular Energies", arXiv:1512.06860v2 [quant-ph], Feb. 4, 2017, 13 pgs.
Peruzzo, Alberto, et al., "A variational eigenvalue solver on a photonic quantum processor", Nature Communications, DOI: 10.1038/ncomms5213, Jul. 23, 2014.
Peruzzo, et al., "A variational eigenvalue solver on a quantum processor", arXiv:1304.3061v2 [quant-ph]; Apr. 10, 2013; 10 pgs.
Peschel, et al., "Entanglement in Solvable Many-Particle Models", arXiv:1109.0159v1 [cond-mat.stat-mech], Sep. 1, 2011, 44 pgs.
Reiner, et al., "Elucidating Reaction Mechanisms on Quantum Computers", arXiv:1605.03590v2 [quant-ph], May 25, 2016, 28 pgs.
Rubin, "A Hybrid Classical/Quantum Approach for Large-Scale Studies of quantum Systems with Density Matrix Embedding Theory", arXiv:1610.06910v1, Oct. 21, 2016, 12 pgs.
Rubin, "A Hybrid Classical/Quantum Approach for Large-Scale Studies of Quantum Systems with Density Matrix Embedding Theory", arXiv:1610.06910v2, Oct. 24, 2016, 10 pgs.
Sawaya, et al., "Error Sensitivity to Environmental Noise in Quantum Circuits for Chemical State Preparation", Journal of Chemical Theory and Computation, ACS Publications, Jun. 2, 2016, 12 pgs.
Scuseria, et al., "An efficient reformulation of the closed-shell coupled cluster single and double excitation (CCSD) equations", J. Chem. Phys. 89(12), Dec. 15, 1988, 6 pgs.
Seeley, et al., "The Bravyi-Kitaev transformation for quantum computation of electronic structure", The Journal of Chemical Physics 137, 224109, Dec. 12, 2012, 16 pgs.
Selinger, et al., "A lambda calculus for quantum computation with classical control", arXiv:cs/0404056v2 [cs.LO], Nov. 2004; 15 pgs.
Shiba, "Magnetic Susceptibility at Zero Temperature for the One-Dimensional Hubbard Model", Physical Review B, vol. 6, No. 3; Aug. 1, 1972, 9 pgs.
Smith, R. S., et al., "A Practical Quantum Instruction Set Architecture", arXiv:1608.03355v2 [quant-ph], Feb. 17, 2017, 15 pages.
Suzuki, "Convergence of General Decompositions of Exponential Operators", Commun. Math. Phys. 163, 491-508, 1994, 18 pgs.
Szabo, et al., "Modern Quantum Chemistry: Introduction to Advanced Electronic Structure Theory", Macmillan Publishing Co., Inc., 1982, 48 pgs.

(56) References Cited

OTHER PUBLICATIONS

Tranter, et al., "The Bravyi-Kitaev Transformation: Properties and Applications", Int'l Journal of Quantum Chemistry 115, 1431-1441, 2015, 11 pgs.
Trotter, "On the Product of Semi-Groups of Operators", Proceedings of the American Mathematical Society 10, 545; 1959, 7 pgs.
Tsuchimochi, et al., "Density matrix embedding in an antisymmetrized geminal power bath", The Journal of Chemical Physics 143, 024107, 2015, 11 pgs.
Wang, et al., "Quantum Simulation of Helium Hydride Cation in a Solid-State Spin Register", ACS NANO, vol. 9, No. 8, 7769-7774, www.acsnano.org, Apr. 23, 2015, 13 pgs.
Wecker, Dave, et al., "Towards Practical Quantum Variational Algorithms", arXiv:1507.08969v2 [quant-ph], Sep. 8, 2015, 11 pages.
Werner, et al., "A second order multiconfiguration SCF procedure with optimum convergence", J. Chem. Phys. 82(11), Jun. 1, 1985, 11 pgs.
Whitfield, James D., et al., "Simulation of Electronic Structure Hamiltonians Using Quantum Computers", arXiv:1001.3855v3 [quant-ph], Dec. 19, 2010, 22 pages.
Wiebe, et al., "Quantum Deep Learning", arXiv:1412.3489v2 [quant-ph]; May 2015; 34 pgs.
Wouters, et al., "A Practical Guide to Density Matrix Embedding Theory in Quantum Chemistry", J.Chem.Theory Comput., May 9, 2016, 14 pgs.
Zheng, Bo-Xiao, et al., "Cluster size convergence of the density matrix embedding theory and its dynamical cluster formulation: a study with an auxiliary-field quantum Monte Carlo solver", arXiv:1608.03316v1 [cond-mat.str-el], Aug. 11, 2016, 14 pgs.
Zheng, et al., "Ground-state phase diagram of the square lattice Hubbard model from density matrix embedding theory", arXiv:1504.01784v3 [cond-mat.str-el], May 21, 2015, 17 pgs.
USPTO, Notice of Allowance dated Sep. 21, 2018, in U.S. Appl. No. 14/822,317, 35 pgs.
KIPO, International Search Report and Written Opinion of the ISA dated Jan. 19, 2018, in PCT/US2017/054421, 10 pgs.
Li, et al., "Hybrid parallel tempering and simulated annealing method", Applied Mathematics and Computation, vol. 212, Issue 1, pp. 216-228, Jun. 1, 2009.
EPO, Extended European Search Report dated Jun. 26, 2020, in EP 17857532.0, 9 pgs.
Kretchmer, et al., "A real-time extension of density matrix embedding theory for non-equilibrium electron dynamics", arXiv:1609.07678v2, Nov. 1, 2017, 15 pgs.

\* cited by examiner
† cited by third party

| U | 2 | 4 | 6 | 8 | 10 |
|---|---|---|---|---|---|
| EXACT | -0.9809782 | -0.68014156 | -0.49157349 | -0.37607898 | -0.30214434 |
| UCCSD | -0.9808687 | -0.67928156 | -0.48543800 | -0.33051713 | -0.02603051 |
| DMET(1)-ED | -0.9951259 | -0.71791138 | -0.54055767 | -0.42535625 | -0.34751768 |
| DMET(2)-ED | -0.9808783 | -0.68014156 | -0.49157349 | -0.37607898 | -0.30214434 |
| DMET(1)-UCCSD | -0.9951259 | -0.71791135 | -0.54055772 | -0.42535622 | -0.34751654 |

SIMULATING QUANTUM SYSTEMS WITH QUANTUM COMPUTATION

CROSS-REFERENCE TO RELATED APPLICATIONS

This application claims priority to U.S. Provisional Application No. 62/402,278 entitled "Simulating Quantum Systems with Quantum Computation" and filed Sep. 30, 2016, which is hereby incorporated by reference.

BACKGROUND

The present disclosure relates to simulating quantum systems with quantum computation.

Techniques for simulating quantum systems on a quantum computer have been proposed. For example, the phase estimation algorithm and the variational quantum eigensolver have been proposed for solving electronic structure problems on a quantum computer.

BRIEF DESCRIPTION OF THE DRAWINGS

FIG. 6 is a table showing data from example calculations.

DETAILED DESCRIPTION

In a general aspect of what is described here, a quantum system is simulated. In some instances, quantum computations executed on one or more quantum processor units (QPUs), which may operate in parallel, are used for density matrix embedding calculations. The quantum computations can include, for example, a variational quantum eigensolver (VQE) used in a density matrix embedding theory (DMET) algorithm or another type of simulation. In some instances, a quantum computer can simulate a quantum system whose Hamiltonian has a larger dimension than that which is provided by the number of qubits available to the quantum computer. In some instances, a hybrid computer system can simulate a quantum system whose Hamiltonian has a larger dimension than that which is provided by the number of qubits available to an individual quantum processor unit (QPU) in the hybrid computer system. The systems and techniques described here may have other advantages in some cases.

Figure 1:
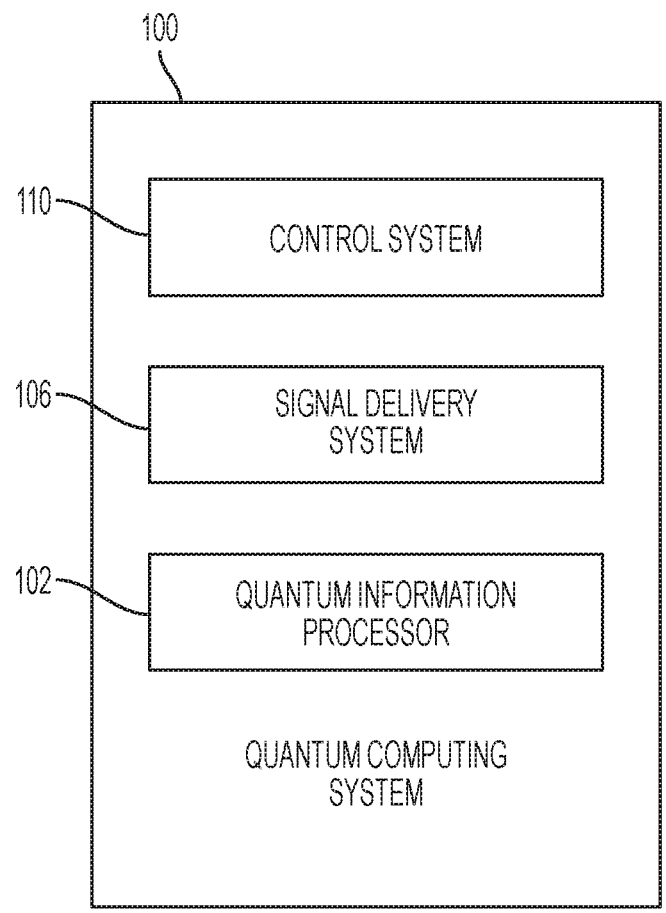
FIG. 1 is a schematic diagram of an example quantum computing system.

FIG. 1 is a schematic diagram of an example quantum computer system 100. The example quantum computer system 100 shown in FIG. 1 includes a control system 110, signal delivery system 106, and a quantum information processor 102. A quantum computing system may include additional or different features, and the components of a quantum computing system may operate as described with respect to FIG. 1 or in another manner.

The example quantum computer system 100 shown in FIG. 1 can perform quantum computational tasks (such as, for example, quantum simulations or other quantum computational tasks) by executing quantum algorithms. In some implementations, the quantum computer system 100 can perform quantum computation by storing and manipulating information within individual quantum states of a composite quantum system. For example, qubits (i.e., quantum bits) can be stored in and represented by an effective two-level sub-manifold of a quantum coherent physical system in the quantum information processor 102.

In some implementations, the quantum computer system 100 can operate using gate-based models for quantum computing. For example, the qubits can be initialized in an initial state, and a quantum logic circuit comprised of a series of quantum logic gates can be applied to transform the qubits and extract measurements representing the output of the quantum computation. In some implementations, the quantum computing system 100 can operate as a quantum annealer or another type of system that uses an adiabatic model for quantum computing. For instance, the qubits can be initialized in an initial state, and the controlling Hamiltonian can be transformed adiabatically by adjusting control parameters to another state that can be measured to obtain an output of the quantum computation.

The example quantum information processor 102 shown in FIG. 1 may be implemented, for example, as a superconducting quantum integrated circuit that includes qubit devices. The qubit devices may be used to store and process quantum information, for example, by operating as ancilla qubits, data qubits or other types of qubits in a quantum algorithm. Coupler devices in the superconducting quantum integrated circuit may be used to perform quantum logic operations on single qubits or conditional quantum logic operations on multiple qubits. In some instances, the conditional quantum logic can be performed in a manner that allows large-scale entanglement within the quantum information processor 102. Control signals may be delivered to the superconducting quantum integrated circuit, for example, to manipulate the quantum states of individual qubits and the joint states of multiple qubits. In some instances, information can be read from the superconducting quantum integrated circuit by measuring the quantum states of the qubit devices. The quantum information processor 102 may be implemented using another type of physical system.

The example quantum information processor 102, and in some cases all or part of the signal delivery system 106, can be maintained in a controlled cryogenic environment. The environment can be provided, for example, by shielding equipment, cryogenic equipment, and other types of environmental control systems. In some examples, the components in the quantum information processor 102 operate in a cryogenic temperature regime and are subject to very low electromagnetic and thermal noise. For example, magnetic shielding can be used to shield the system components from stray magnetic fields, optical shielding can be used to shield the system components from optical noise, thermal shielding and cryogenic equipment can be used to maintain the system components at controlled temperature, etc.

In the example shown in FIG. 1, the signal delivery system 106 provides communication between the control system 110 and the quantum information processor 102. For example, the signal delivery system 106 can receive control signals from the control system 110 and deliver the control signals to the quantum information processor 102. In some instances, the signal delivery system 106 performs preprocessing, signal conditioning, or other operations to the control signals before delivering them to the quantum information processor 102.

In some implementations, the signal delivery system 106 includes connectors or other hardware elements that transfer signals between the quantum information processor and the control system 110. For example, the connection hardware can include signal lines, signal processing hardware, filters, feedthrough devices (e.g., light-tight feedthroughs, etc.), and other types of components. In some implementations, the connection hardware can span multiple different temperature and noise regimes. For example, the connection hardware can include a series of temperature stages that decrease between a higher temperature regime (e.g., at the control system 110) and a lower temperature regime (e.g., at the quantum information processor 102).

In the example quantum computer system 100 shown in FIG. 1, the control system 110 controls operation of the quantum information processor 102. The example control system 110 may include data processors, signal generators, interface components and other types of systems or subsystems. Components of the example control system 110 may operate in a room temperature regime, an intermediate temperature regime, or both. For example, the control system 110 can be configured to operate at much higher temperatures and be subject to much higher levels of noise than are present in the environment of the quantum information processor 102.

In some implementations, the control system 110 includes a classical computing system that executes software to compile instructions for the quantum information processor 102. For example, the control system 110 may decompose a quantum logic circuit or quantum computing program into discrete control operations or sets of control operations that can be executed by the hardware in the quantum information processor 102. In some examples, the control system 110 applies a quantum logic circuit by generating signals that cause the qubit devices and other devices in the quantum information processor 102 to execute operations. For instance, the operations may correspond to single-qubit gates, two-qubit gates, qubit measurements, etc. The control system 110 can generate control signals that are communicated to the quantum information processor 102 by the signal delivery system 106, and the devices in the quantum information processor 102 can execute the operations in response to the control signals.

In some cases, the control system 110 includes one or more classical computers or classical computing components that produce a control sequence, for instance, based on a quantum computer program to be executed. For example, a classical processor may convert a quantum computer program (e.g., instructions written in the Quil programming language) to an instruction set for the native gate set or architecture of the quantum information processor 102. In some cases, the control system 110 includes a microwave signal source (e.g., an arbitrary waveform generator), a bias signal source (e.g., a direct current source) and other components that generate control signals to be delivered to the quantum information processor 102. The control signals may be generated based on a control sequence provided, for instance, by a classical processor in the control system 110. The example control system 110 may include conversion hardware that digitizes response signals received from the quantum information processor 102. The digitized response signals may be provided, for example, to a classical processor in the control system 110.

In some cases, the quantum computer system 100 includes multiple quantum information processors 102 that operate as respective quantum processor units (QPU). In some cases, each QPU can operate independent of the others. For instance, the quantum computer system 100 may be configured to operate according to a distributed quantum computation model, or the quantum computer system 100 may utilize multiple QPUs in another manner. In some implementations, the quantum computer system 100 includes multiple control systems, and each QPU may be controlled by a dedicated control system. In some implementations, a single control system can control multiple QPUs; for instance, the control system 110 may include multiple domains that each control a respective QPU.

In some instances, the quantum computer system 100 uses multiple QPUs to execute multiple unentangled quantum computations (e.g., multiple variational quantum eigensolvers) that collectively simulate a single quantum mechanical system. As an example, the unentangled quantum computations may collectively perform part of a density matrix embedding calculation, and multiple variational quantum eigensolvers may be used to simulate respective fragments in the density matrix embedding calculation.

Figure 2:
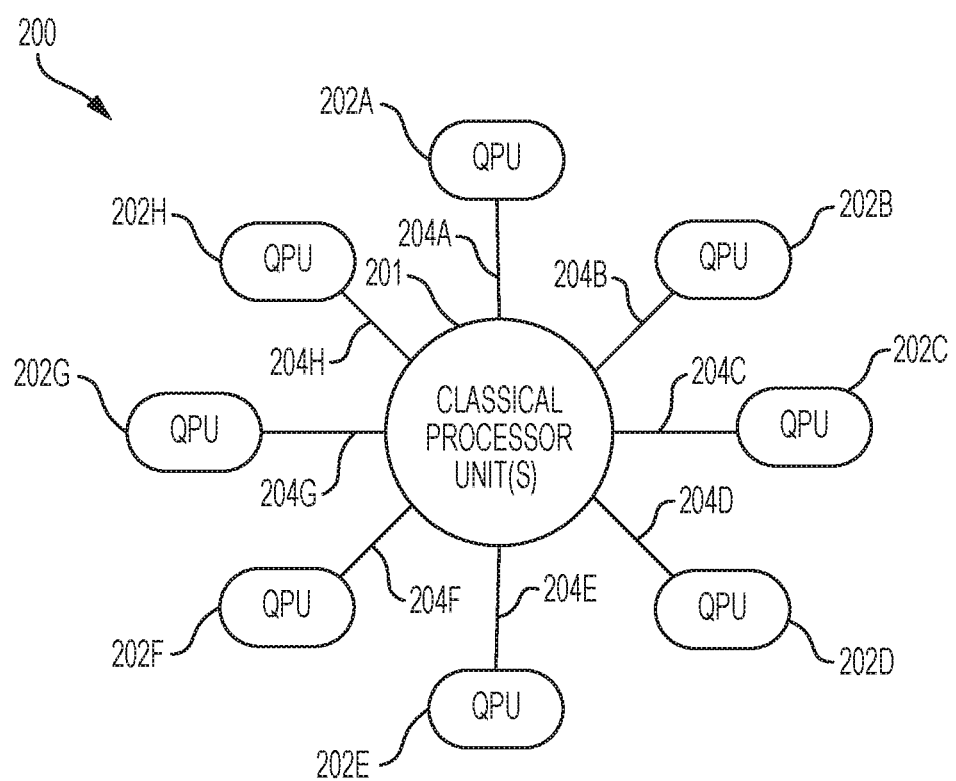
FIG. 2 is a schematic diagram of an example computing system that includes multiple quantum processor units (QPUs).

FIG. 2 is a schematic diagram of an example computer system 200 that includes multiple quantum processor units (QPUs). The example computer system 200 may be implemented as a distributed computing system, for example, with QPUs operating in disparate locations; or the QPUs may operate in proximity to each other, for example, in a common facility or structure.

The example computer system 200 shown in FIG. 2 includes one or more classical processor unit(s) 201 communicably connected with eight quantum processor units 202A, 202B, 202C, 202D, 202E, 202F, 202G, 202H (collectively, the "QPUs 202"). The example computer system 200 may include another number of QPUs (e.g., less than eight, or tens or hundreds of them). The classical processor unit(s) 201 communicate with the QPUs 202 through the respective interfaces 204A, 204B, 204C, 204D, 204E, 204F, 204G, 204H (collectively, the "interfaces 204"). The computer system 200 may include additional or different components, and the components may be arranged as shown in FIG. 2 or in another manner.

The classical processor unit(s) 201 may be implemented using various types of classical computational resource, for example, one or more general purpose microprocessors that can run applications and programs by executing or interpreting software, scripts, functions, executables, and other types of computer program code. In some cases, the classical processor unit(s) 201 can be implemented on a dedicated chip or chipset, or it can be integrated with other devices on a shared chip. In some implementations, the classical processor unit(s) 201 can be or include a single-core processor, a multi-core processor that includes multiple processing units, or one or more commercially-available products.

One or more of the classical processor unit(s) 201 may operate as a host device that can control operation of the QPUs 202. For instance, the host device can operate as a master device that delegates processing tasks to the QPUs and controls timing and dataflow in the computer system 200. For example, the host device may identify QPUs to execute individual sub-processes in an algorithm (e.g., executions of a VQE in a DMET algorithm), and the host device may delegate the sub-process to the QPUs, for instance, by sending associated instructions to the respective QPUs. In some cases, the sub-process delegated to each QPU represents a particular sub-problem of a large quantum system that is being simulated in the computer system 200; the sub-problems can be computed by the QPUs and then reintegrated into the total solution by the classical processor unit(s) 201. For example, the classical processor unit(s) 201 may provide sub-problems that have been constructed according to density matrix embedding theory (DMET).

In some instances, the QPUs can operate as specialized processors that are configured to supplement functionality of the classical processor unit(s) 201, for example, in simulations of quantum systems. A co-processor can include hardware, firmware, or other features configured to execute a class of operations or a class of functions faster or otherwise more efficiently than the main processor. In some implementations, the computer system 200 includes the QPUs 202 and multiple other distinct types of computing modules, such as, for example, FPGAs, application-specific integrated circuits (ASICs), systems-on-chip (SoCs) or other processor devices. Operation of the QPUs and other devices can be supervised or otherwise controlled by one or more of the classical processor unit(s) 201.

Each of the example QPUs 202 includes qubit devices that define the computational state of that QPU. In the example shown in FIG. 2, the QPUs 202 operate as unentangled units, which means that none of the QPUs 202 becomes entangled with any of the other QPUs 202 during operation of the computer system 200. For example, the QPU 202A does not become entangled with any of the other QPUs 202B, 202C, 202D, 202E, 202F, 202G, 202H during operation of the computer system 200. Although qubit devices within the same QPU can become entangled with each other, qubit devices not within the same QPU cannot become entangled with each other during operation of the example computer system 200.

In the example shown in FIG. 2, each QPU 202 can include any type of data processing hardware device that can encode and process information in quantum states of light or matter. In some cases, QPUs can be configured to execute quantum algorithms that perform certain computational tasks more efficiently than other types of processors. Some QPUs can be configured to implement a variational quantum eigensolver (VQE), perform a Fourier transform, factor large integers (e.g., Shor's algorithm), simulate a quantum system, perform a search (e.g., Grover's algorithm), estimate quantum phases, or other types of computational tasks. In some examples, QPUs are configured to perform these and other types of operations by leveraging large-scale entanglement and other quantum resources.

In some cases, one or more of the QPUs 202 includes a superconducting circuit, and the qubit devices are implemented as circuit devices that include Josephson junctions, for example, in superconducting quantum interference device (SQUID) loops or other arrangements, and are controlled by radio-frequency signals, microwave signals, and bias signals delivered to the quantum processor cell 102. In some cases, one or more of the QPUs 202 includes an ion trap system, and the qubit devices are implemented as trapped ions controlled by optical signals delivered to the system. In some cases, one or more of the QPUs 202 includes a spin system, and the qubit devices are implemented as nuclear or electron spins controlled by microwave or radio-frequency signals delivered to the system. The QPUs 202 may be implemented based on another physical modality of quantum computing.

In some aspects of operation, one or more of the classical processor unit(s) 201 accesses a computer program to be executed in the computer system 200. The computer program can include computer program code that defines variables and data processing tasks (e.g., functions, routines, etc.). The computer program can be executed in the computer system 200 by delegating data processing tasks to the various processor devices. The data processing tasks may be delegated in series, in parallel, or both, as specified by the computer program or other protocols. For instance, the classical processor unit(s) 201 may delegate computational tasks to the QPUs 202 in series, in parallel, as the QPUs 202 become available, or otherwise.

In some instances, instructions generated by the classical processor unit(s) 201 are configured to cause one of the QPUs 202 to perform a particular function or other data processing task defined in the computer program. The instructions are provided to the QPU 202 through the appropriate interface 204, and the QPU 202 performs the data processing task by executing the instructions generated by the classical processor unit(s) 201. Output values generated by the QPU can then be provided back to the classical processor unit(s) 201 through the interface 204. The classical processor unit(s) 201 can then execute or delegate further operations in the computer program based on the output values from the QPU.

The computer program (which may also be called a program, script, or code) includes computer program code that can be written in any form of programming language, including compiled or interpreted languages, declarative or procedural languages, and it can be deployed in any form, including as a stand-alone program or as a module, component, subroutine, object, or other unit suitable for use in the computer system 200. A computer program may, but need not, correspond to a file in a file system. A program can be stored in a portion of a file that holds other programs or data (e.g., one or more scripts stored in a document), in a single file dedicated to the program in question, or in multiple coordinated files (e.g., files that store one or more modules, sub-programs, or portions of code).

The interfaces 204 can include, for example, connectors, wires, cables, communication interfaces, networks or other systems or components to transfer information between the classical processor unit(s) 201 and the respective QPUs 202. In some cases, the interfaces 204 are implemented as all or part of the signal delivery system 106 in FIG. 1. For instance, the interfaces 204 may connect the respective QPUs 202 to a control system that includes the classical processor unit(s) 201. In some cases, the interfaces 204 may include one or more wired or wireless connections, or one or more wired or wireless networks or other communication channels. For example, the classical processor unit(s) 201 may communicate with the respective QPUs 202 over one or more public or private networks (a Local Area Network (LAN), a Wide Area Network (WAN), a Virtual Private Network (VPN), the Internet, a peer-to-peer network, a cellular network, a Wi-Fi network, or another type of data network).

In some aspects of operation, the computer system 200 simulates a quantum system. For example, the computer system 200 may perform the quantum simulation process 400 shown in FIG. 4, or the computer system 200 may simulate a quantum system in another manner. In some instances, the computer system 200 utilizes the QPUs 202 in a simulation that executes a density matrix embedding theory (DMET) algorithm. A wide variety of Hamiltonians and quantum systems can be simulated using DMET algorithms. In some cases, the accuracy of a DMET algorithm generally increases with larger fragment sizes, and utilizing the QPUs 202 may increase the size of fragments that can be simulated in the DMET algorithm. Moreover, by using multiple QPUs in parallel, calculations can be accelerated for faster simulation times.

In some aspects of operation, the classical processor unit(s) 201 parameterizes a quantum algorithm for execution by a QPU based on the hardware and performance capabilities of the particular QPUs 202 that are available in the system 200. In some instances, the classical processor unit(s) 201 identifies fragments for simulation by particular QPU hardware resources. For example, the classical processor unit(s) 201 may parallelize a simulation into M =8 fragments to be executed by the M =8 QPUs available in the system. In some cases, the classical processor unit(s) 201 parallelizes a simulation into a larger number of fragments to be executed in multiple iterations of parallel iteration by the M =8 QPUs available. As another example, each of the QPUs may have a different number of qubits available, with the i-th QPU having $N_i$-qubit computational power. In such cases, the classical processor unit(s) 201 may define fragments that utilize the full computing power of each QPU. As such, the classical processor unit(s) 201 can identify fragments having a dimension that is matched to the computing resources (e.g., number of qubits) of each respective QPU. These and other techniques can be used to adapt a quantum simulation to the specific hardware (including the specific size, speed, and resources of each QPU) available in the computing system 200.

Figures 3A, 3B:
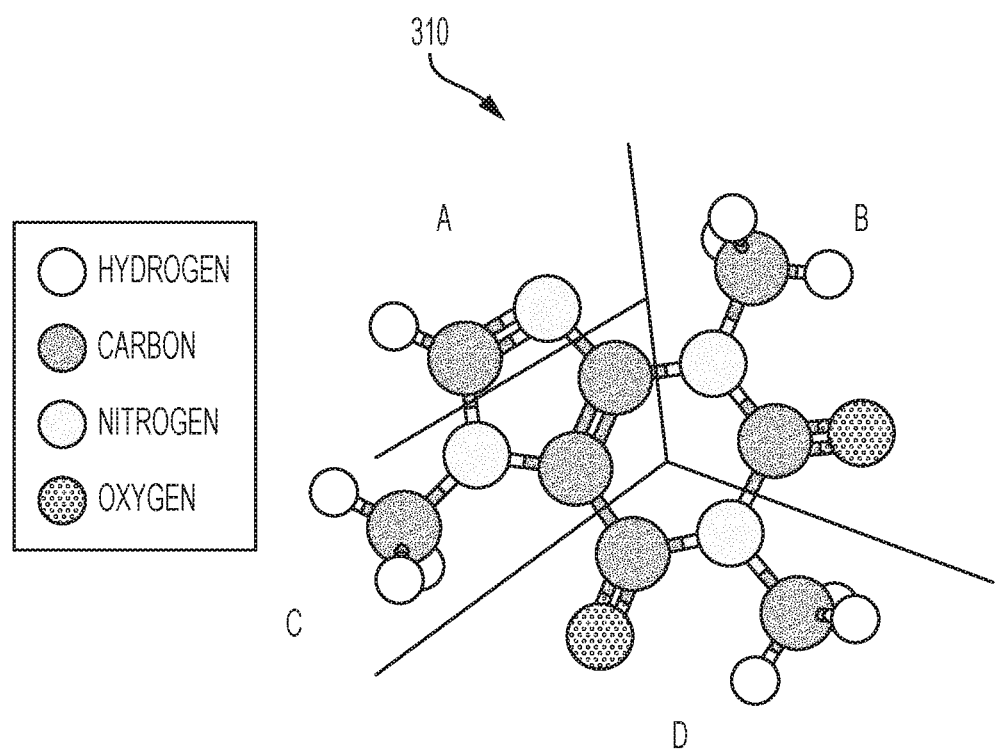
FIG. 3A is a schematic representation of an example quantum system that includes multiple fragments.
FIG. 3B is a diagram of an example quantum system that includes multiple fragments.

FIG. 3A is a schematic representation of an example quantum system 300 that includes multiple fragments. The quantum system 300 can be, for example, a large N-body quantum system that has been discretized into 'r' distinct fragments. In the example shown in FIG. 3A, the total system is segmented into r=16 fragments. Each fragment may represent a quantum subsystem within the total quantum system 300; for example, the portion labeled F1, includes part of the total quantum system 300 and may be referred to as a fragment.

A fragment may represent any subspace within a Hilbert space defined by the quantum system 300. In the example shown, none of the fragments overlaps another fragment in the quantum system 300, and the fragments collectively constitute the entire quantum system 300. In some cases, each fragment corresponds to a subset of bodies or properties (e.g., spins, electrons, photons, nuclei, protons, neutrons, etc.) within a quantum system, or a fragment may correspond to another type of quantum subsystem within the larger quantum system. In some cases, the fragments can be defined based on a type of problem to be solved by a simulation of the quantum system; chemical, structural or physical properties of the quantum system; or other considerations.

FIG. 3B is a diagram of an example quantum system 310 that includes multiple fragments. The example quantum system 310 shown in FIG. 3B is a single caffeine molecule. The caffeine molecule is an arrangement of hydrogen atoms, carbon atoms, nitrogen atoms, and oxygen atoms. As shown in FIG. 3B, a discretization process has identified four fragments in the quantum system 310; the fragments, labeled 'A', 'B', 'C', and 'D' are of unequal sizes. In the example shown in FIG. 3B, each fragment corresponds to a region containing bonded atomic species within the structure of the caffeine molecule.

Figure 4:
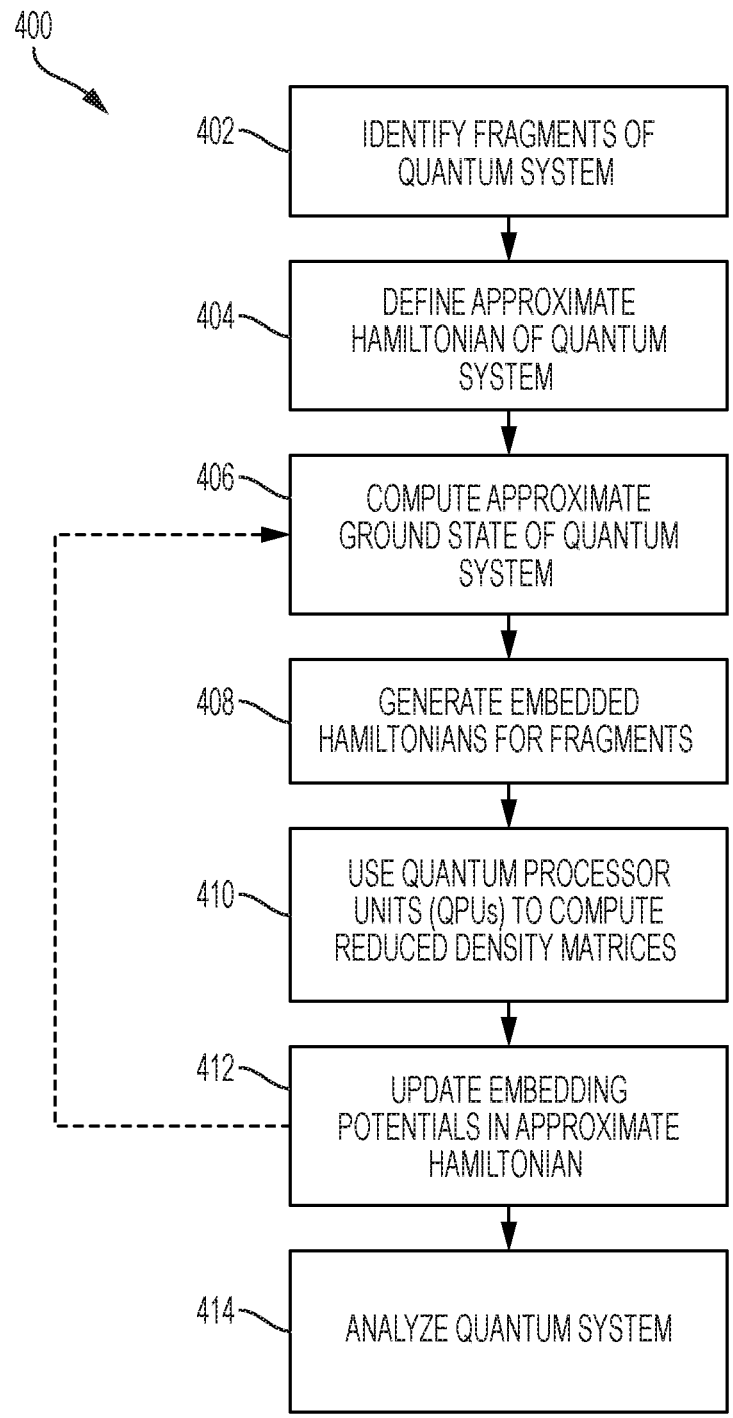
FIG. 4 is a flow chart showing an example quantum simulation process.

FIG. 4 is a flow chart showing an example quantum simulation process 400. In some examples, the process 400 performs a density matrix embedding procedure that is executed using variational quantum eigensolvers (VQEs) running on one or several quantum computing systems or QPUs. In some cases, the process 400 may represent another type of simulation procedure.

The example process 400 shown in FIG. 4 may include additional or different operations, and the operations may be performed in the order shown or in another order. In some instances, an individual operation in the process 400 may be implemented as one or more sub-processes, or multiple operations in the process 400 may be performed in parallel or implemented together as a single sub-process. In some cases, operations are repeated in an iterative fashion, for example, until a terminating condition is reached.

The example process 400 can be used to simulate a quantum system. In some examples, the quantum system to be simulated is a sub-atomic, atomic or molecular system. For example, the quantum system to be simulated can be all or part of the caffeine molecule shown in FIG. 3B. In some cases, the quantum system is one- or two-dimensional lattice model, an extended chemical system, or a ground state or transition state molecule. In some cases, the process 400 can be used to simulate a black hole event horizon, an open quantum system coupled to an environment, a topological quantum computer, or a quantum annealer. Other types of systems may be simulated by the example process 400.

The example process 400 can be executed by a computer system that includes one or more quantum processor units (QPUs) and possibly additional processor units. For example, the process 400 may be executed by the quantum computer system 100 shown in FIG. 1, the computer system 200 shown in FIG. 2 or another type of computer system. In some cases, a classical processor unit in the computer system runs the process 400 and uses one or more QPUs to perform certain operations. For example, a classical processor unit may use a QPU to perform an operation by sending instructions to the QPU. The classical processor unit may use other types of processors as well (e.g., a graphics processing unit (GPU), a cryptographic co-processor, or another type of classical co-processor).

In some implementations of the process 400, a quantum system is simulated by operating a set of models on a computer system that includes a classical processor unit and a plurality of unentangled quantum processor units (QPUs). In some cases, the classical processor unit operates a low-level quantum system model (e.g., $\hat{H}_{chem}$ or another Hamiltonian), for instance, to compute an approximate ground state at 406. In some cases, the unentangled QPUs operate high-level quantum subsystem models (e.g., $\{\hat{H}_{emb}\}$ or another set of Hamiltonians), for instance, to compute reduced density matrices (RDMs) for fragments at 410. Multiple subsystem models may be operated in parallel, for example, by using multiple unentangled QPUs concurrently. The computer system may operate the set of models in another manner in some cases.

In some examples, a server or server cluster has access to several quantum computing systems, where each quantum computing system includes a superconducting microwave quantum circuit that can execute quantum algorithms. The server or server cluster includes classical processors (e.g., commercial microprocessors) that perform classical computing operations in the process 400 (e.g., operations 402, 404, 406, 408, 412, 414) and delegates (at 410) quantum computing operations to the quantum computing systems. The server or server cluster may communicate with the quantum computing systems, for example, over a Wide Area Network (WAN), a Virtual Private Network (VPN) or another type of network configuration. As such, the server or server cluster may access and utilize quantum computing resources over a large geographic region in some cases. When one of the quantum computing systems receives instructions from the server or server cluster, the control system of the quantum computing system compiles QPU-level instructions that cause the superconducting microwave quantum circuit to execute the delegated quantum algorithm. After the quantum computing system generates an output by executing the quantum algorithm, the quantum computing system sends the output to the server or server cluster. The server or server cluster can then process the outputs from multiple quantum computing systems.

In some examples, a control system in a quantum computing system has access to several QPUs within the quantum computing system, where each QPU includes a superconducting microwave quantum circuit that can execute quantum algorithms. The control system includes classical processors (e.g., commercial microprocessors) that perform classical computing operations in the process 400 (e.g., operations 402, 404, 406, 408, 412, 414) and identifies (at 410) specific QPUs to perform quantum computing operations. The control system may be located with the QPUs in a controlled environment, and may communicate with the QPUs, for example, over transmission lines or another type of microwave connection. When the control system identifies a QPU to execute a quantum algorithm, the control system compiles QPU-level instructions that cause the superconducting microwave quantum circuit of the QPU to execute the quantum algorithm. The control system can have multiple quantum algorithms executed by the QPUs, for example, in parallel or in a designated order. The control system can then process the outputs from multiple QPUs.

At 402, fragments of a quantum system are identified. The fragments can be identified, for example, by discretizing the quantum system into subparts as shown in FIGS. 3A and 3B, or the fragments may be identified in another manner. The fragments can be defined, for instance, by projection operators (e.g., as in Equation (11) or otherwise) or the fragments can be defined in another manner. In some examples, each fragment is a single site (or multiple sites) of a lattice model. In some examples, each fragment is a localized atomic orbital corresponding to a piece of a larger molecular basis set. The fragments can be identified based on known attributes of the quantum system being simulated, based on the type or output of the simulation, or based on other information.

In some instances, fragments are identified at 402 based on the quantum computing resources available. As an example, the number of fragments identified may be based on (e.g., less than, equal to, an integer multiple of, etc.) the number of QPUs available. As another example, the size of the fragments may be based on the size of the QPUs available. For instance, the process 400 may identify fragments of the largest size that can be simulated by the QPUs available, or the process may identify fragments of multiple sizes matched to the sizes of multiple available QPUs.

At 404, an approximate Hamiltonian of the quantum system is defined. An example of an approximate Hamiltonian is the Hamiltonian $\hat{H}_{chem}$ shown in Equation (4); in some cases, an approximate Hamiltonian may have another form. The approximate Hamiltonian can be or include a quadratic Hamiltonian. For example, the approximate Hamiltonian may include the Hartree-Fock Hamiltonian $\hat{F}_{chem}$ shown in Equation (4) below, which may be augmented by additional terms or values. The approximate Hamiltonian can include embedding potentials, which may be defined, for example, as the embedding potentials $v_{r,s}$ in Equation (4) below or in another manner. The approximate Hamiltonian can also include a global chemical potential in some cases. When the approximate Hamiltonian is defined, initial values can be assigned to the embedding potentials. For instance the initial values assigned to the embedding potentials can be zeros, random values, estimated values, etc. In some cases, initial values are assigned to a global chemical potential in the approximate Hamiltonian as well.

At 406, an approximate ground state of the quantum system is computed. The approximate ground state can be computed, for example, by performing a low-level simulation on a classical or quantum processor based on the approximate Hamiltonian. The approximate ground state can be, for example, the Slater determinant wavefunction $|\phi\rangle$ for the full quantum system with the Hartree-Fock Hamiltonian augmented with the embedding potentials.

At 408, embedded Hamiltonians are generated for the fragments. The embedded Hamiltonians can be generated as described with respect to Equation (16) below, or the embedded Hamiltonians can be generated in another manner. In some cases, each embedded Hamiltonian represents the approximate Hamiltonian rotated or projected onto one of the respective fragments.

In the example process 400 shown in FIG. 4, operations 402, 404, 406, 408 generate a set of models that are used to simulate the quantum system. The set of models can include a low-level system model for the full quantum system as well as higher-level subsystem models for the respective fragments of the full quantum system. The approximate Hamiltonian (e.g., $\hat{H}_{chem}$) defined at 404, which includes embedding potentials (e.g., $v_{r,s}$) associated with the respective fragments, is an example of a low-level system model for the quantum system; and the embedded Hamiltonians (e.g., $\hat{H}_{emb}$) generated at 408 are examples of quantum subsystem models for the respective fragments. Another set of models may be generated for simulating a quantum system, or the example set of models described in the example process 400 may be generated in another manner.

At 410, quantum processor units (QPUs) are used to compute reduced density matrices (RDMs). In some examples, the 1-reduced density matrix (1-RDM) and 2-reduced density matrix (2-RDM) are computed for each fragment based on the embedded Hamiltonian for the fragment. Some or all of the RDMs can be computed concurrently by operating multiple QPUs in parallel. In some cases, two or more of the RDMs are computed at different times, for example, by running two simulations in series on a single QPU. In some cases, the QPUs generate the set of values $\{D_{r,s}^x\}$ in Equation (19) below, or the QPUs may produce other types of outputs.

In some implementations, multiple unentangled QPUs are used at 410, and a variational quantum eigensolver (VQE) algorithm is executed on each QPU to compute the reduced density matrices (RDMs) for the respective fragments based on the quantum subsystem models. For example, one-particle reduced density matrices (1-RDMs), two-particle reduced density matrices (2-RDMs), or both may be computed by the VQE algorithm.

At 412, the embedding potentials in the approximate Hamiltonian are updated. In some cases, an updated set of values for the embedding potentials can be computed based on the RDMs computed (at 410) by the QPUs, and the embedding potentials in the approximate Hamiltonian may then be updated (e.g., by assigning the updated set of values to the embedding potential variables in the approximate Hamiltonian). The updated set of values can be calculated, for example, using a cost function or another type of minimization function. For instance, the updated set of values may be calculated according to Equation (19) below, or another type of cost function may be used to compute updated values.

In some implementations, the example simulation process 400 includes an iterative process, and each iteration of the iterative process can include one or more of operations 406, 408, 410, 412. For example, a current iteration of the iterative process may include computing an updated approximate ground state for the current iteration (406) based on the approximate Hamiltonian (with embedding potentials having been updated on a prior iteration, in some cases); generating updated quantum subsystem models (e.g., updated embedded Hamiltonians) for the current iteration (408) based on the updated approximate ground state; using the QPUs to compute updated RDMs based on the updated quantum subsystem models (410); and updating the embedding potentials in the approximate Hamiltonian (412) based on the updated RDMs.

In some cases, one or more checks are performed at 412; the checks may be performed within the sub-process or calculation that updates the embedding potentials, or the checks may be performed by a separate sub-process or calculation, for instance, before or after updating the embedding potentials. In some cases, the RDMs are analyzed to check whether particles are conserved. In some cases, the current values of the embedding potentials are compared to prior values of the embedding potentials to check whether the values have changed (increased or decreased) by more than a threshold (e.g. zero or a non-zero threshold).

Results of checks or other calculations performed at 412 can determine whether the process 400 returns to 406 (e.g., for another iteration of the iterative process), progresses to 414, or proceeds in another manner. For example, if it is determined that particles are not conserved, the global chemical potential may be updated, and the process 400 can return to 406 for another iteration. As another example, if the embedding potentials have changed by more than a threshold (e.g. zero or a non-zero threshold), the process 400 can return to 406 for another iteration with the updated values of the embedding potentials. If particles are conserved and the embedding potentials have not changed (e.g., by more than the threshold value), then the process 400 can proceed to 414. Other types of checks may be performed in some cases.

At 414, the quantum system is analyzed. The analysis may include computing an observable or other physical property of the quantum system. The observable or other physical property may be computed based on the RDMs generated at 410 (e.g., on the last iteration), based on the approximate Hamiltonian with the updated values assigned to the embedding potentials, or based on other information. In some examples, an approximate ground state energy of the quantum system may be computed from the RDMs computed at 410. Additional or different physical properties of the quantum system (e.g., dipole moments, electron polarizability, charge and spin-correlation functions) may be computed from the RDMs in some cases.

In some implementations, ground state energies of quantum systems can be determined by quantum or hybrid classical/quantum techniques. For instance, small-scale devices may be leveraged to identify important subspaces of relatively large Hamiltonians. In the following discussion, we describe an example embedding scheme, density matrix embedding theory (DMET), that fits with the output from the variational quantum eigensolver (VQE) and other hybrid approaches. This approach is validated using a quantum abstract machine simulator that reproduces the ground state energy of the Hubbard model converged to the infinite limit.

The variational quantum eigensolver (VQE) can be implemented as a hybrid classical/quantum algorithm to approximate the ground state eigenvalues and density matrices of a Hamiltonian. In some cases, the VQE can be implemented as a classical optimization loop invoking a quantum abstract machine (QAM) used for state preparation and operator measurement. Recent work investigating this approach yielded quantum circuits for ansatz state preparation that are short and demonstrated that the algorithm is potentially robust to standard noise models.

The VQE using a wavefunction ansatz that is exponentially expensive on a classical computer, such as unitary coupled-cluster or approximate Hamiltonian evolution, offers a potentially advantageous alternative to other high fidelity solvers (e.g., FCI, density matrix renormalization group, etc.) for active space calculations and embedding schemes.

In some cases, the VQE can be integrated into computational chemistry methodologies that utilize a high-fidelity solver with an interface utilizing the one-particle and two-particle reduced density matrices (1-RDM and 2-RDM, respectively).

Density matrix embedding theory (DMET) maps the problem of finding the ground state of a large N-particle system onto many interacting impurity problems. This can be achieved by self-consistently matching the 1-RDM from a low-level wavefunction for the entire system with the 1-RDMs of the impurities calculated with a high-level technique. Though it is not necessarily clear that such an iterative scheme would result in accurate local RDMs, DMET has been demonstrated to be highly accurate for one- and two-dimensional lattice models, extended chemical systems, and for ground state and transition state molecules. Furthermore, spectral functions (on the real-frequency axis) are accessible from DMET without any bath discretization error allowing for the construction of arbitrary dynamic correlation functions. These studies demonstrate the amazing quality of DMET with modestly sized impurities.

DMET algorithms include an embedded problem solver. In some implementations, the problem solver produces a high-accuracy 1-RDM for the embedded problem such that the fragment piece of the mean-field 1-RDM can be matched to the correlated 1-RDM for the fragment. In this discussion, we propose the use of VQE for the embedded problem solver (as an alternative to FCI or DMRG routines). Among other possible advantages, using the VQE as the embedded problem solver potentially allows for (i) the study of a larger embedding Hamiltonian, allowing access to longer range correlation functions, and (ii) accelerating the DMET algorithm by quickly finding the solution to the embedded problem on a quantum computer. As a proof of principle, we determine the ground state energy of the repulsive-U Hubbard model for small rings and the thermodynamic limit.

In this section of the discussion, we review density matrix embedding techniques and discuss how such techniques can incorporate a VQE algorithm as an embedded Hamiltonian solver.

For a large system Q, its wavefunction can be arbitrarily bi-partitioned into a fragment (or impurity) and bath (or environment). Some examples of a fragment include a single site or multiple sites of a lattice model or localized atomic orbitals corresponding to a piece of a larger molecular basis set. The total wavefunction $|\psi\rangle$ may be expressed in the tensor product of basis states of the fragment and the bath, {|a⟩⊗|b⟩}, which has a linear dimension of $d_A \times d_B$ where $d_A := \dim A$ (resp. $d_B := \dim B$) is the dimension of the Hilbert space of the A fragment (resp. B bath). Utilizing the Schmidt decomposition, an eigenstate of Q can be written as a sum over the tensor products of the Schmidt basis states.

$$|\psi\rangle = \sum_a^{d_A} \sum_b^{d_B} \psi_{a,b}|a\rangle|b\rangle \qquad (1)$$

$$= \sum_a^{d_A} \sum_b^{d_B} \sum_\alpha^{\min(d_A,d_B)} U_{a,\alpha} \lambda_\alpha V_{\alpha,b}^\dagger |a\rangle|b\rangle$$

$$= \sum_\alpha^{\min(d_A,d_B)} \lambda_\alpha |\tilde{a}_\alpha\rangle|\tilde{b}_\alpha\rangle.$$

This Schmidt basis is constructed by the singular value decomposition of the coefficient tensor. This reformulation demonstrates that there is a local fragment basis and environment basis of the same size that produces an equivalent representation of $|\psi\rangle$. Without loss of generality, we can assume the Hilbert space of the fragment is smaller than the environment. In the Schmidt basis, no matter how large the bath, a fragment A can entangle with $d_A$ bath states. The Schmidt states can be used to project the Hamiltonian into a combined impurity/bath basis that has the same ground state as the original Hamiltonian but is significantly smaller in size $$\hat{H} \to \sum_{a,a',b,b'} |ab\rangle\langle ab|\hat{H}|a'b'\rangle\langle a'b'|. \qquad (2)$$

For a general large-scale quantum system, the wavefunction $|\psi\rangle$ can be computed approximately. This constraint naturally leads to the fundamental approximation in DMET: the embedded Hamiltonian is approximated by constructing bath states from the Schmidt decomposition of the ground state of an approximate (e.g., quadratic) Hamiltonian for the total system. As a consequence, the embedded Hamiltonian now contains an interacting fragment embedded in a non-interacting bath. The embedding Hamiltonian may be approximated by matching the fragment's 1-RDM with the low-level mean-field density matrix of the system by varying the embedding potential that appears in the quadratic Hamiltonian.

In this section of the discussion, we describe an example low-level quadratic Hamiltonian. For an arbitrary chemical system, the Hamiltonian contains terms that are at most four creation/annihilation operators corresponding to one-and two-particle interactions:

$$\hat{H}_{chem} = \sum_{i,j} {}^1h_{i,j}\hat{a}_i^\dagger \hat{a}_j + \frac{1}{2}\sum_{ij,kl} {}^2V_{ij,kl}\hat{a}_i^\dagger \hat{a}_j^\dagger \hat{a}_l \hat{a}_k. \qquad (3)$$

To vary the form of the bath states used when constructing the embedded Hamiltonian, a potential may be added to the full chemical Hamiltonian. In some cases, the augmented total system Hamiltonian is then approximated using the Hartree-Fock method to find an optimal single-particle basis, for example:

$$\hat{H}_{chem} \to \hat{F}_{chem} + \sum_{r,s} v_{r,s}\hat{a}_r^\dagger \hat{a}_s. \qquad (4)$$

In this section of the discussion, we describe bath orbitals determined from a slater determinant. Another example way to construct the fragment and bath embedding states that is similar to the Schmidt decomposition in Equation (1) is a contraction over the bath basis:

$$|\psi\rangle = \sum_{a,b} \psi_{a,b}|a\rangle|b\rangle \qquad (5)$$

$$= \sum_a |a\rangle \left(\sum_b \psi_{a,b}|b\rangle\right) \qquad (6)$$

$$= \sum_a |a\rangle|\tilde{a}\rangle, \qquad (7)$$

where $$|\tilde{a}\rangle \approx \sum_b \psi_{a,b}|b\rangle.$$

Orthogonalizing $\{|\tilde{a}\rangle\}$ into a set of states $\{|a'\rangle\}$ gives:

$$|\psi\rangle = \sum_{a,a'} \psi_{a,a'}|a\rangle|a'\rangle. \qquad (8)$$

Note that while each $|a'\rangle \in B$, there are no more than dim A of them. With this form for the embedding basis, the form of the bath states constructed from the mean-field wavefunction can be found. This may be achieved, for example, by projecting the occupied states with overlap on the fragment onto the environment orbitals and normalizing.

There are no formal restrictions on the low-level wavefunction representing the total system Q, though in some cases it is desirable that one can quickly construct an approximate eigenfunction of Q. Alternative approximate wavefunctions that have been used are the antisymmetrized geminal power wavefunctions that introduce some correlation into the bath, products of Bogoliubov quasi-particle states, and a Slater determinant. The following is a derivation of the embedding basis from a Slater determinant wavefunction. This low-level wavefunction for the full system $|\phi_0\rangle$ can be expressed as the product of fermionic operators in the occupied subspace acting on the true vacuum:

$$|\phi_0\rangle = \left(\prod_p \hat{a}_p^\dagger\right)|vac\rangle \qquad (9)$$

The single particle orbitals $\hat{a}_p^\dagger$ can be constructed from linear combinations of site orbitals, $\hat{c}^{554}$, in the lattice:

$$\hat{a}_p^\dagger = \sum_\mu D_{\mu,p}\hat{c}_\mu^\dagger. \qquad (10)$$

Here, the matrix D corresponds with the Hartree-Fock transform from local lattice spin-orbitals to the basis that minimizes the Hartree-Fock Hamiltonian of the system. A rotation to the fragment and bath basis can be constructed in a similar manner to the canonical orthogonalization of atomic orbitals that appears in the Hartree-Fock procedure applied to molecules.

The overlaps of the occupied orbitals projected onto the fragment space can be calculated using a fragment projection operator $\hat{P}_F := |\mu\rangle\langle\mu|$ acting on the occupied set of orbitals indexed by p and q:

$$S = \langle \hat{P}_F \phi_p | \hat{P}_F \phi_q \rangle \quad (11)$$
$$= \langle \phi_p | \hat{P}_F^\dagger \hat{P}_F | \phi_q \rangle$$
$$= \langle \phi_p | \hat{P}_F | \phi_q \rangle.$$

The eigenvectors of this overlap matrix correspond to an orbital rotation that forms the fragment and bath basis. Diagonalizing S with a unitary V gives $$\Delta := V^\dagger S V = \text{diag}(\Delta_1 \ldots, \Delta_{d_A}). \quad (12)$$

Naturally, the eigenvalues of the overlap matrix are between 0 and 1. Zero eigenvalues correspond to occupied states that have zero overlap on the fragment. The bath states can be constructed by projecting the occupied orbitals with overlap on the fragment into the bath:

$$|b_i\rangle = \sum_p \frac{V_{p,i}^*}{\sqrt{1-\Delta_i}} \hat{P}_B |\phi_p\rangle. \quad (13)$$

Finally, the rotation C to the Schmidt basis can be defined by the direct sum of the bath transformation and an identity matrix of dimension equal to the number of orbitals on the fragment, $n_F$:

$$C := I_{n_F} \oplus B = \text{diag}(I_{n_F}, B). \quad (14)$$

The core states with zero overlap on the fragment can be eliminated from the embedded Hamiltonian by including their interaction at the mean-field level similar to generating an active space interacting with a frozen set of core states.

The embedded Hamiltonian may then be constructed by projecting into the fragment and bath states:

$$\hat{H}_{emb} := P\hat{H}P \quad (15)$$

which, for a Slater determinant wavefunction, corresponds to a single- and double-particle integral transform:

$$\hat{H}_{emb} = \sum_{p,q} {}^1\tilde{h}_{p,q} \hat{a}_p^\dagger \hat{a}_q + \frac{1}{2} \sum_{p,q;r,s} {}^2\tilde{V}_{p,q;r,s} \hat{a}_p^\dagger \hat{a}_q^\dagger \hat{a}_s \hat{a}_r, \quad (16)$$

where $${}^1\tilde{h}_{p,q} := C^{\dagger\,1}h_{a,b}C + f_{pq}^{core} \quad (17)$$
$${}^2\tilde{V}_{p,q;r,s} := (C \otimes C)^{\dagger\,2} V_{a,b;c,d}(C \otimes C). \quad (18)$$

In the above transformation, $f^{core}$ is the interaction with the non-entangled non-overlapping core states, C is a matrix from Equation (14) whose columns are the transformation vectors to the embedding basis, and $^1h$ and $^2V$ are the one- and two-particle integral tensors defined in the lattice basis.

The following section of the discussion relates to determining improved (e.g., optimal) values for the embedding potentials. The DMET procedure can include operations to improve the bath states so they approximate the bath states of the true embedded Hamiltonian. Schmidt bath state tuning may be achieved by varying the potential that was added to the system Hamiltonian in Equation (4). Variation in this potential can provide a connection between the embedded Hamiltonian and the quadratic Hamiltonian representing the larger quantum system.

Some example implementations of the DMET procedure can be summarized in the following three sub-processes or operations:

First, find the ground state Slater determinant wavefunction $|\phi\rangle$ for the full quantum system Q with the Hartree-Fock Hamiltonian augmented with the embedding potential.

Second, for all fragments, use the Slater determinant wavefunction $|\phi\rangle$ to construct the embedding basis and project the system Hamiltonian into each embedded Hamiltonian. Then solve for the 1-RDM and 2-RDM with a high-level technique (e.g., VQE or another high-level technique).

Third, adjust the embedding potential in the mean-field Hamiltonian such that the 1-RDM of the impurity calculated with the high-level wavefunction matches the 1-RDM calculated from the quadratic Hamiltonian.

The first, second and third sub-processes can be repeated, for example, until particle conservation and the embedding potential do not change between iterations.

The third sub-process can be carried out, for instance, by minimizing the squared norm between the fragment piece of the mean-field 1-RDM and the fragment 1-RDM computed from the ground state wavefunction for the embedded Hamiltonian:

$$CF_{frag}(u) = \sum_x \sum_{r,s \in frag} (D_{r,s}^x - D_{r,s}^{mf}(u))^2. \quad (19)$$

Here, the variable u may represent the embedding potentials $v_{r,s}$ in Equation (4), and least squares minimization or another minimization technique can be used to minimize $CF_{frag}$ with respect to $v_{r,s}$. This cost function is known as the fragment-only density matrix fitting. Alternatives such as full matching of the 1-RDMs in the embedding basis or matching the electron densities on the fragment have also been studied.

The exponentially scaling FCI has prompted studying alternative methods for finding the correlated ground state 1-RDM. Though this may not lead to an optimal approximation to the embedded Hamiltonian fragment and bath states it does allow for the study of significantly larger fragments, which may be important for assessing longer range correlation functions and more accurate local expectation values. The ability to study larger fragments at higher fidelity has many implications for accurate simulations of materials and chemistry. For example, if one were studying a reaction center in a metal-organic framework, a fragment would likely contain the metal site and ligand orbitals for an accurate description of the energy and properties. The VQE can be used when solving for the 1-RDM and 2-RDM of the embedded Hamiltonian. DMET's use of the 1-RDM of the embedded Hamiltonian makes VQE a suitable algorithm for this use case.

The VQE provides a functional minimization scheme that can leverage fast construction of a wavefunction to find expectation values of operators. The energy E of the system can be minimized by varying over parameters for the wavefunction ansatz:

$$E = \min_\theta \langle \psi(\theta) | \hat{H} | \psi(\theta) \rangle. \quad (20)$$

The expectation value can be determined by summing the expectation of each term in the Hamiltonian:

$$\langle \hat{H} \rangle = \sum_k \langle \hat{H}_k \rangle. \quad (21)$$

For a general quantum chemical Hamiltonian, k scales quadratically with respect to basis set size. To evaluate the Hamiltonian expectation value, the wavefunction $|\Psi(\theta)\rangle$ can be prepared many times with a subsequent measurement of the $\hat{H}_k$ operator. In the examples described below, the unitary coupled cluster (UCC) state is used as the function for the energy functional, though others could be considered, such as, for example, the variational adiabatic ansatz.

UCC is a many-body expansion wavefunction ansatz parameterized by the cluster coefficients associated with each generator. We use the UCC-singles-doubles ansatz corresponding to anti-Hermitian generators performing single- and double-particle excitations $$|\psi(\theta)\rangle = \exp\left(\sum_{k=1}^{2} T_k(\theta)\right) |\psi_{ref}\rangle \quad (22)$$

where:

$$T_1(\theta) \approx \sum_{a,i} \theta_a^i (\hat{a}_i^\dagger \hat{a}_a - \hat{a}_a^\dagger \hat{a}_i) \quad (23)$$

$$T_2(\theta) \approx \sum_{a,b;i,j} \theta_{a,b}^{i,j} (\hat{a}_i^\dagger \hat{a}_a \hat{a}_j^\dagger \hat{a}_b - \hat{a}_b^\dagger \hat{a}_j \hat{a}_a^\dagger \hat{a}_i). \quad (24)$$

In a quantum computing application, the antisymmetric fermionic creation/annihilation operators can be represented by distinguishable qubits. We utilize the Jordan-Wigner transformation (JW) for mapping fermionic creation/annihilation operators to Pauli spin-operators that preserve the anti-commutation relations and parity of the second quantized operators in Equation (25). The representation of second quantized operators in Pauli matrices by the JW transform scales linearly in the number of Pauli terms as the basis index is increased. (There are alternatives such as the Bravyi-Kitaev transformation that have logarithmic scaling when representing second quantized operators.) The maps can be defined as $$\hat{a}_q^\dagger \mapsto (\otimes_{i<p} \sigma_i^z) \sigma_p^+$$

$$\hat{a}_q \mapsto (\otimes_{i<p} \sigma_i^z) \sigma_p^-, \quad (25)$$

where:

$$\sigma_\pm := \tfrac{1}{2}(\sigma^x \mp i\sigma^y). \quad (26)$$

For each shot of the VQE algorithm, the wavefunction of the system —according to a UCC ansatz—can be constructed by first preparing the Hartree-Fock reference, O(n) in the number of gates to prepare the state where n is the number of orbitals, then evolving the initial wavefunction according to Equation (22), using $O(n^4)$ in the number of gates for the exponentiation of the unitary generators.

The 1-RDM and 2-RDM can be measured after an optimal set of θ parameters are determined by measuring n(n+1)/2 expectation values corresponding to the 2-RDM:

$$^2D_{kl}^{ij} = \langle \psi | \hat{a}_i^\dagger \hat{a}_j^\dagger \hat{a}_b \hat{a}_k | \psi \rangle. \quad (27)$$

The 1-RDM can be obtained by contraction from the 2-RDM:

$$^1D_i^j = \frac{1}{n-1} \sum_a {}^2D_{i,a}^{j,a}. \quad (28)$$

The fragment 1-RDM of the total system can be matched to the fragment piece of the 1-RDM obtained from the VQE algorithm, for example, by varying the embedding potential in Equation (3).

Unlike the classical cluster operators that commute at all orders, the unitary coupled cluster operators in Equation (23) and Equation (24), henceforth denoted as τ, do not commute with each other at all orders. Therefore, approximating the exponential by a particular order of the Suzuki-Trotter decomposition may be important for constructing accurate distributions. The anti-Hermitian generators do not commute because the de-excitation operators $—a_a^{554} a_i$ do not commute with the excitation operators. This can be seen for the first order τ operators. Here we use a, b to denote the particle space and i, j to denote the hole space.

$$[\tau_i^a, \tau_j^b] = [(\hat{a}_a^\dagger \hat{a}_i - \hat{a}_i^\dagger \hat{a}_a), (\hat{a}_b^\dagger \hat{a}_j - \hat{a}_j^\dagger \hat{a}_b)] \quad [29]$$

$$= [\hat{a}_a^\dagger \hat{a}_i, \hat{a}_b^\dagger \hat{a}_j] + [\hat{a}_j^\dagger \hat{a}_b, \hat{a}_a^\dagger \hat{a}_i] + [\hat{a}_b^\dagger \hat{a}_j, \hat{a}_i^\dagger \hat{a}_a] + [\hat{a}_i^\dagger \hat{a}_a, \hat{a}_j^\dagger \hat{a}_b] \quad [30]$$

The first and last commutators vanish while the middle two terms survive when there is an overlapping index in $\tau_1^a$ and $\tau_j^b$:

$$[\hat{a}_j^\dagger \hat{a}_b, \hat{a}_a^\dagger \hat{a}_i] = \delta_{b,a} \hat{a}_j^\dagger \hat{a}_i - \delta_{j,i} \hat{a}_a^\dagger \hat{a}_b \quad (31)$$

$$[\hat{a}_b^\dagger \hat{a}_j, \hat{a}_i^\dagger \hat{a}_a] = \delta_{i,j} \hat{a}_b^\dagger \hat{a}_a - \delta_{b,a} \hat{a}_j^\dagger \hat{a}_j. \quad (32)$$

As a result, Trotter error is considered when generating circuits for UCC state preparation. Below, we discuss the performance of UCCSD with Trotter orders 1 and 2 with Trotter steps beyond 1. (Here, the term "Trotter order" refers to the order of the series approximation to the exponential of two non-commuting operators; and the term "Trotter steps" refers to the number of slices that each order is broken into in order to minimize the correction term.)

In our example calculations, we considered the one-dimensional Hubbard model with repulsive-U interactions and anti-periodic boundary conditions as a representative test system for DMET.

$$\hat{H} = -t \sum_{\langle i,j \rangle} \left( \hat{a}_{i,\sigma}^\dagger \hat{a}_{j,\sigma} + h.c. \right) + U \sum_i \hat{a}_{i,\alpha}^\dagger \hat{a}_{i,\beta}^\dagger \hat{a}_{i,\beta} \hat{a}_{i,\alpha} \quad (33)$$

The DMET self-consistency loops were run using the QC-DMET code with an interface to PySCF for exact diagonalization of the embedded Hamiltonian. The VQE algorithm for solving the embedded Hamiltonian used Quil and Rigetti Computing's pyQuil package to construct the UCCSD ansatz and evolved the wavefunction on a noiseless quantum virtual machine. All UCCSD-VQE runs started with a second-order Møller-Plesset perturbation theory guess for the cluster amplitudes and utilized about 20 iterations of BFGS with the gradient numerically approximated. For single-site DMET calculations the low-level and high-level fragment density matrices were equivalent and thus the DMET loop only involved setting the chemical potential such that the number of electrons in each fragment summed to the total system's electron count. For two-site models the fragment 1-RDM was generally not equal to the fragment Slater determinant 1-RDM and thus utilized a numerical search for the optimal embedding potential.

Figure 5:
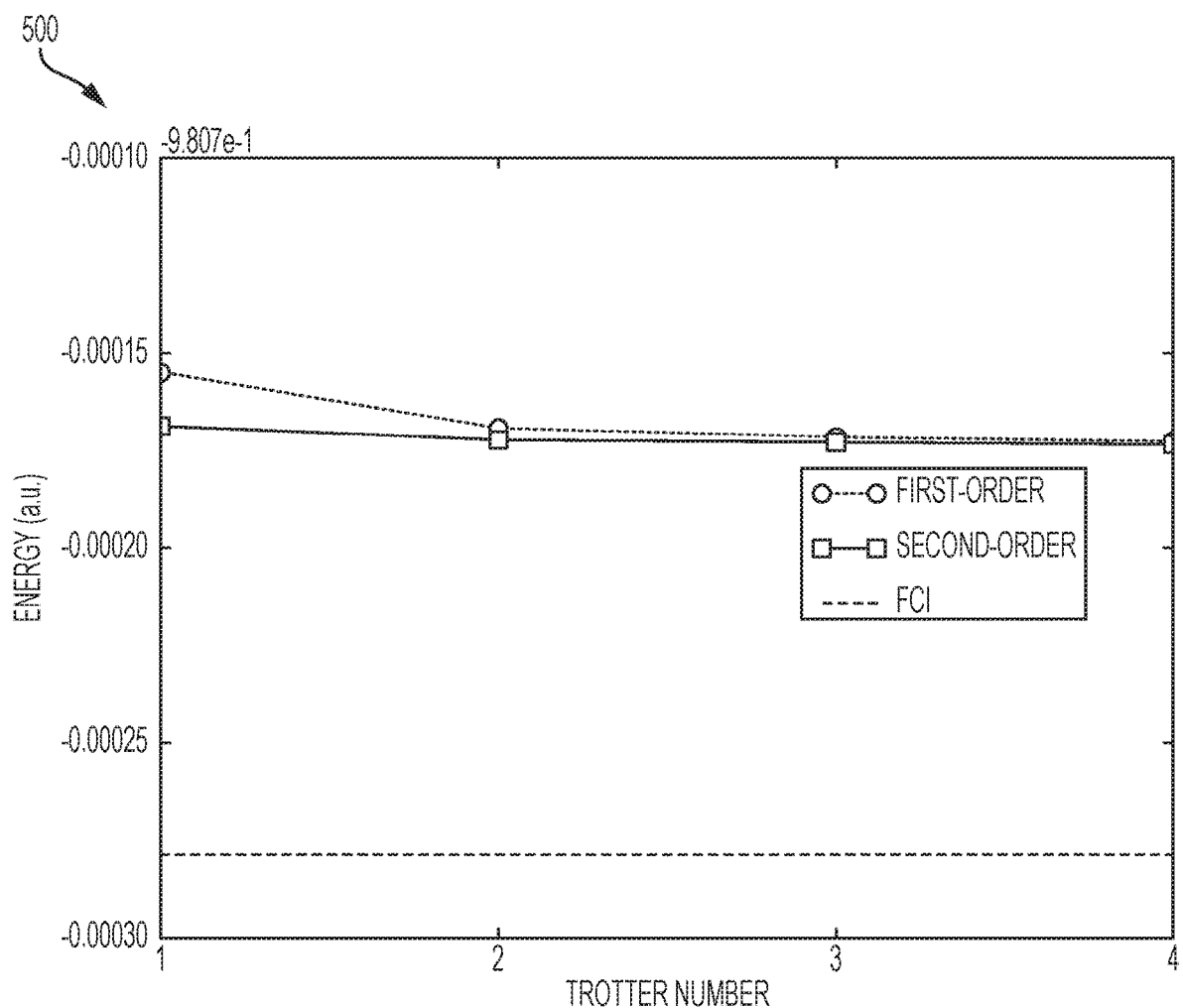
FIG. 5 is a plot showing the energy-per-site from example calculations.

FIG. 5 is a plot 500 showing energy-per-site from the example calculations for Trotter steps 1, 2, 3, and 4. The plot 500 shows energy-per-site of the four-site Hubbard model with $U/|t|=2$ with anti-periodic boundary conditions calculated with Trotter orders 1 and 2 with Trotter steps 1, 2, 3, and 4. The error between Trotter steps of Suzuki-Trotter orders is generally hundredths of a milli-Hartree indicating that the significant gap between FCI and UCCSD is based on the wavefunction ansatz.

The non-commuting nature of the cluster operators do not drastically affect the accuracy of the UCCSD ansatz. FIG. 5 shows the convergence of the energy-per-site as the Trotter order and Trotter steps are increased for $U/|t|=2$. Trotter order and Trotter steps indicate the structure of the wavefunction ansatz for UCCSD. For example, the first order Trotter with N -Trotter steps produces an ansatz of form:

$$|\psi\rangle = (e^{\hat{\tau}_s/N} e^{\hat{\tau}_d/N})^N \qquad (34)$$

where $\tau_s$ and $\tau_d$ correspond to the single and double anti-Hermitian generators with their coefficients which are described in Equation (23) and Equation (24). The persistence of the energy gap as Trotter order and Trotter steps are increased demonstrates that the single reference nature and the truncated set of generators are the main sources of error.

In some implementations, the DMET technique can introduce three sources of error: (i) the fragment size and thus the number of non-interacting bath states that can entangle with the fragment, (ii) the embedded Hamiltonian solver, and (iii) the pieces of the embedded Hamiltonian 1-RDM that are chosen to match for updating the embedding potential. The effects of (i) and (ii) can be determined by studying small lattices and comparing the ground state energy against the FCI solution and the full UCCSD solution.

FIG. 6 is a table 600 showing data from example calculations. In particular, the table 600 in FIG. shows energy-per-site of the half-filled Hubbard model for a four-site ring with anti-periodic boundary conditions evaluated with DMET using one- and two-site fragments. The exact solution is computed with an exact diagonalization of the Hamiltonian. Both Trotter order and Trotter steps were equal to one for all calculations shown.

The table 600 shown in FIG. 6 compares the ground state energy-per-site of a four-site ring at various interaction strengths between the FCI solution, the UCCSD solution, and various fragment sizes for DMET. The DMET solutions are labeled by DMET(n), where n is the number of sites considered in the fragment, followed by an acronym for the type of embedded solver—for example, ED corresponds to FCI. The accuracy of the UCCSD solution to the four-site-ring lattice generally decreases as U is increased demonstrating the expected result that singles and doubles generators cannot parametrize the full unitary group. In this example, a four-site lattice requires eight-spin-orbitals and thus eight qubits. The UCCSD ansatz contains 14 cluster amplitudes when restricting the wavefunction to the singlet subspace. Under a greedy parallelization of commuting instructions for breaking the unitary evolution into time steps, a single state evolution at first order Trotter involves 1422 time steps where multiple qubit operations are performed at each step. Each time step has an average of 0.8692 one-qubit gates and 0.8101 two-qubit gates. The coupled-cluster reference is usually chosen in a basis where the one-particle piece of the Hamiltonian is diagonal. For the Hubbard model this involves a Fourier transform on the one-particle and two-particle integral tensors resulting in m one-body terms and $m^3$ two-body terms where m is the number of lattice sites. The two-body terms are proportional to U/N.

A single fragment site results in a trivial two-orbital embedded Hamiltonian. For this example, UCCSD+VQE is equivalent to FCI, CISD, and CCSD solvers. Considering a two-site DMET at $U/|t|=2$ and $U/|t|=8$ produced energies-per-site of −0.9809165 and −0.35446392, respectively. Though not exactly equal to the DMET(2)-ED result, the error is on the order of the difference between the UCCSD solution for the full lattice and the FCI solution for the full lattice.

Figure 7:
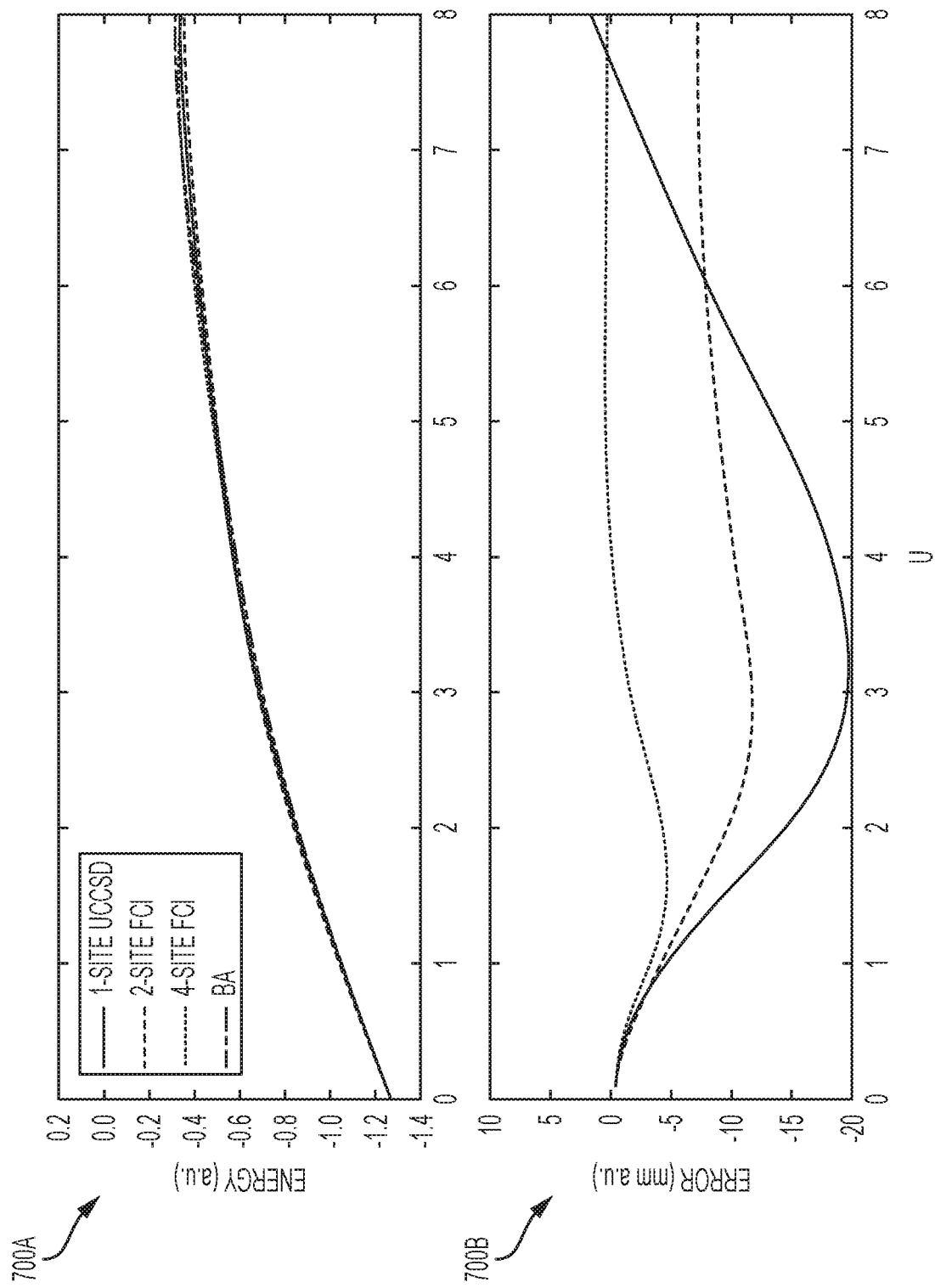
FIG. 7 is a pair of plots showing the energy-per-site and error from example calculations.

FIG. 7 is a pair of plots 700A, 700B showing the energy-per-site and error from example calculations. In FIG. 7, we plot the energy-per-site for a 100-site lattice calculated with DMET and the Bethe ansatz, with a one-, two-, and four-impurity sites in the DMET scheme. FCI represents the exact diagonalization solution to the single impurity site problem. Plot 700A in FIG. 7 demonstrates that DMET(1)-UCCSD method converges to the correct solution at high-U. Plot 700B in FIG. 7 shows the energy difference between the Bethe ansatz solution and the DMET solutions, which is represented as the error for DMET(1)-ED, DMET(1)-UCCSD, DMET(2)-ED, and DMET(4)-ED relative to the Bethe ansatz. As expected, the error decreases significantly as the number of sites increases, and the quality of the solution improves as fragment size is increased. An m site fragment utilizes 4m qubits (for each embedded Hamiltonian eigenvalue problem) and thus classical simulations are restricted to small fragment sizes.

For at least some types of systems, hybrid classical/quantum computation models fit well with certain techniques for studying the electronic structure of molecules and materials. Some techniques involve selecting an active space or embedded piece of the Hamiltonian to treat at higher fidelity. These techniques can be especially important when describing the electronic structure of correlated materials and molecules such as metal-oxides, heterogeneous catalysis, multi-electron redox reactions, and catalysts. In contrast to exact diagonalization solvers commonly used in impurity or active space problems, quantum computation offers a technique to treat these Hamiltonians with high accuracy in polynomial time.

In some implementations, a DMET algorithm operates by mapping the problem of finding the N-particle ground state of a large system to many smaller interacting impurity problems. Therefore, DMET is applicable to very large scale problems be it either molecules or materials. Unlike DMFT that requires the frequency dependent two-particle Green's function, DMET utilizes the 1-RDM of the embedded problem with high accuracy. This makes DMET and the VQE an advantageous combination in many instances. The 1-RDM and 2-RDM may be computed at each iteration of the VQE optimization.

The VQE algorithm can be implemented as a general functional minimization routine that allows for the use of any quantum state preparation method. In our calculations, we utilized the UCC ansatz and demonstrated that despite the non-commuting nature of the generators, the error for the ansatz comes from the truncation of the series and not Trotter error. Therefore, at least in the case of simulating local interaction models, low-order Trotter approximation and Trotter number are sufficient for accurate state preparation.

In some aspects of what we have described, classical techniques for describing quantum chemistry or correlated materials can be accelerated with a hardware quantum processing unit (QPU). Many of the classical methods that utilize a 1-RDM or 2-RDM of an active space can be integrated with the VQE algorithm or other hybrid classical/quantum techniques. Further integration can lead to methodologies to study large quantum systems with higher resolution than what is currently possible with state of the art classical methods.

In this work, execution of quantum programs was done using the quantum abstract machine and Quil, its quantum instruction language. In the following discussion, we outline elements of this quantum programming environment, including examples of techniques used to compute the 1-RDM and 2-RDM.

The VQE can be implemented as a classical optimizer around a quantum execution unit. For example, a classical optimization loop may produce the next $\theta$ parameters of Equation (20) for minimization. Mathematically, $\theta$ parameterizes a wavefunction ansatz, but computationally, they are regarded as parameters to generate a new quantum program. These programs are run on a quantum execution unit modeled as a restricted quantum abstract machine $\mathfrak{W} = (|\Psi\rangle\Delta, C, G, G', P, \kappa)$ with $$G = \left\{ \sigma^x, \sigma^y, \sigma^z, H, \frac{1}{\sqrt{2}}\begin{pmatrix} 1 & \pm i \\ \pm i & 1 \end{pmatrix}, CNOT \right\}, \quad (35)$$

$$G' = \{R_z\}. \quad (36)$$

Here, the machine $\mathfrak{W} = (|\Psi\rangle\Delta, C, G, G', P, \kappa)$ represents a machine with quantum state $|\Psi\rangle$, classical state C, static gates G, parametric gates G', program P, and program counter $\kappa$. In Equations (35) and (36), the gates are understood to be the collection of operators acting on each qubit combination of the quantum state $|\Psi\rangle$. The classical memory C is as large as $\log_2 \dim |\Psi\rangle$—the number of qubits—to hold the z-basis measurements for each loop of the VQE, which are collected to approximate $\rangle\hat{H}\rangle$. Alternatively, by using a quantum virtual machine, the amplitudes of $|\Psi\rangle$ can be observed in the computational basis and $\rangle\hat{H}\rangle$ can be computed directly.

The object of interest to simulate can be specified in terms of sums of fermionic operations, such as the Hamiltonian in Equation (16). After a fermionic transform such as in Equation (25), said object can be represented as a sum of products of Pauli spin operators. We represent these Pauli sums algebraically as first-class objects in a canonical form. We wish to compute a program which acts identically to the exponentiation of this Pauli representation—as in Equation (22)—on the quantum abstract machine's $|\Psi\rangle\Delta$ Exponentiating a Pauli sum includes two steps: factorization via Trotterization, and exponentiation of Pauli terms. Consider the Pauli terms $$A = 2\,\sigma_0^x \sigma_1^x,$$

$$B = -\tfrac{1}{2}\sigma_0^x \sigma_2^z. \quad (37)$$

These are represented as objects in Python using the pyQuil library:

```
> A = 2.0*PauliTerm('X',0)*PauliTerm('X',1)
> B = -0.5*PauliTerm('X',0)*PauliTerm('Z',2)
> print "A =", A, "\nB =", B
A = 2.0*X0*X1
B = -0.5*X0*Z2
```

Exponentiation of a Pauli term has three parts: a change to the $|\pm\Delta$basis, an entanglement of the qubits on which the operator non-trivially acts, and a rotation about z. For example, we can see this by looking at a Quil program which allows one to compute the action of $e^A$.

```
> print exponentiate(A)
H 0
H 1
CNOT 0 1
RZ(4.0) 1
CNOT 0 1
H 0
H 1
```

This Quil program itself is also a first-class object. Indeed, the result of a Suzuki-Trotter approximation of, say, $e^{A+B}$ combines programs which compute $e^A$ and $e^B$. We can see this by looking at the Quil program which computes $e^{A+B}$ in a first-order decomposition:

```
> print trotterize(A, B)
H 0
H 1
CNOT 0 1
RZ(4.0) 1
CNOT 0 1
H 0
H 1
H 0
CNOT 0 2
RZ(-1.0) 2
CNOT 0 2
H 0
```

Quil programs are written as a serial list of instructions, but in fact the semantics are not changed if the order between successive commuting instructions is changed. As such, we can think of such instructions occurring in a single time slice. (If the n-th commuting instruction executes in $t_n$ time, then the time slice itself executes in $\max_n t_n$ time and is the worst case for arbitrary $t_n$ with maximal parallelization. If all $t_n$ are known for each time slice, then it is possible to do aggressive parallelization by overlapping commuting instructions from subsequent time slices, despite the time slices as a whole (its action on the total Hilbert space) being non-commuting.) A straight-line Quil program itself is parallelized if it is transformed according to a maximal semantics-preserving parallelization. Consider the following 16-instruction sample from a state evolution according to the UCCSD ansatz with first-order Trotter and one time slice for the four-site Hubbard model:

```
            X 2
            X 3
            H 3
            RX(1.5707963267948966) 5
            CNOT 3 4
            CNOT 4 5
            RZ(0.00001) 5
            CNOT 4 5
            CNOT 3 4
            H 3
            RX(-1.5707963267948966) 5
            RX(1.5707963267948966) 1
            H 5
            CNOT 1 2
            CNOT 2 3
            CNOT 3 4
```

Instruction sequences like X 2 and X 3 commute and may execute in the same time slice. However, X 3 and H 3 do not commute, and they execute in different time slices. The parallelized Quil program is as follows:

```
    Time Slice #1:     X 2
                       X 3
                       RX(1.5707963267948966) 5
                       RX(1.5707963267948966) 1
    Time Slice #2:     H 3
                       CNOT 1 2
    Time Slice #3:     CNOT 3 4
    Time Slice #4:     CNOT 4 5
    Time Slice #5:     RZ(0.00001) 5
    Time Slice #6:     CNOT 4 5
    Time Slice #7:     CNOT 3 4
                       RX(-1.5707963267948966) 5
    Time Slice #8:     H 3
                       H 5
    Time Slice #9:     CNOT 2 3
    Time Slice #10:    CNOT 3 4
```

The 16-instruction straight-line program has been reduced to a 10-time-slice program averaging 0.9 one-qubit gates and 0.7 two-qubit gates per time slice. All instructions being equal, this gives a 38% improvement in timing.

When a final Quil program is prepared through the various means described, it is dispatched to a representation of a QAM: either a hardware QPU or a software quantum virtual machine. In the examples described above, a remotely deployed quantum virtual machine was used for all Quil execution.

In a general aspect, a computer system simulates a quantum system.

In a first aspect, a set of models representing a quantum system is generated, and the quantum system is simulated by operating the set of models on a computer system. The set of models includes subsystem models representing respective fragments of the quantum system. The computer system includes a classical processor unit and a plurality of unentangled quantum processor units (QPUs). Operating the set of models includes using the unentangled QPUs to operate the respective subsystem models.

Implementations of the first aspect may include one or more of the following features. Operating the set of models can include using two or more of the unentangled QPUs to operate two or more of the subsystem models in parallel. Simulating the quantum system can include using density matrix embedding theory (DMET) to compute an approximate ground state energy for the quantum system.

Implementations of the first aspect may include one or more of the following features. Using the unentangled QPUs to operate the respective subsystem models comprises executing a variational quantum eigensolver (VQE) algorithm on each QPU to compute reduced density matrices (RDMs) for the respective fragments; for example, one-particle reduced density matrices (1-RDMs), two-particle reduced density matrices (2-RDMs), or both may be computed by the VQE algorithm. An approximate ground state energy of the quantum system can be computed from the RDMs.

In some example implementations of the first aspect, the set of models includes an approximate Hamiltonian (e.g., $\hat{H}_{chem}$) for the quantum system; the approximate Hamiltonian includes embedding potentials (e.g., $v_{r,s}$) associated with the respective fragments; the subsystem models are embedded Hamiltonians (e.g., $\hat{H}_{emb}$) for the respective fragments, and the QPUs compute the RDMs based on the embedded Hamiltonians. Simulating the quantum system can include, by operation of the classical processor unit: computing an approximate ground state of the quantum system based on the approximate Hamiltonian having an initial set of values assigned to the embedding potentials; and computing an updated set of values for the embedding potentials based on the RDMs computed by the QPUs. Simulating the quantum system can include an iterative process, and each iteration of the iterative process can include computing an approximate ground state of the quantum system for the iteration based on the approximate Hamiltonian; generating subsystem models for the iteration based on the approximate ground state for the iteration; by operation of the unentangled QPUs, computing updated RDMs for the respective fragments based on the updated subsystem models; and computing an updated set of values for the embedding potentials based on the updated RDMs. The approximate Hamiltonian may then be updated, for example, by assigning the updated set of values to the embedding potentials in the approximate Hamiltonian. The simulation may include calculating an approximate ground state energy of the quantum system, for example, from the updated RDMs.

In a second aspect, fragments of a quantum system to be simulated are identified. One or more quantum processor units (QPUs) are used to generate reduced density matrices (RDMs) for the respective fragments. An approximate ground state energy of the quantum system is computed based on the RDMs.

Implementations of the second aspect may include one or more of the following features. Multiple RDMs may be generated in parallel by multiple unentangled QPUs, with each of the RDMs being generated by a respective one of the unentangled QPUs. Each of the RDMs may be generated by a variational quantum eigensolver (VQE) algorithm executed by the one or more QPUs.

Implementations of the second aspect may include one or more of the following features. An approximate Hamiltonian (e.g., $\hat{H}_{chem}$) representing the quantum system can be defined. The approximate Hamiltonian can include embedding potentials (e.g., $v_{r,s}$) associated with the respective fragments. An approximate ground state of the quantum system can be computed based on the approximate Hamiltonian having an initial set of values assigned to the embedding potentials. Embedded Hamiltonians (e.g., $\hat{H}_{emb}$) can be defined for the respective fragments based on the approximate ground state. The one or more QPUs can be used to generating the RDMs based on the embedded Hamiltonians. An updated set of values for the embedding potentials can be computed based on the RDMs.

In a third aspect, a quantum simulation method includes: identifying fragments (F) of a quantum system (Q) to be simulated, each fragment representing a quantum subsystem of the quantum system to be simulated; defining an approximate Hamiltonian ($\hat{H}_{chem}$) for the quantum system, the approximate Hamiltonian comprising embedding potentials ($v_{r,s}$) for the respective fragments; by operation of a classical processor unit, solving for a first approximate ground state |φ⟩ of the quantum system based on the approximate Hamiltonian having a first set of values assigned to the embedding potentials; defining an embedded Hamiltonian ($\hat{H}_{emb}$) for each fragment of the quantum system based on the first approximate ground state of the quantum system; computing, by operation of one or more quantum processor units (QPUs), reduced density matrices (RDMs) for the fragments based on the embedded Hamiltonians, wherein each RDM is generated by a variational quantum eigensolver (VQE) executed by one of the one or more QPUs; computing a second set of values for the embedding potentials based on the RDMs, wherein the second set of values is computed by minimizing a cost function; and solving for a second approximate ground state of the quantum system based on the approximate Hamiltonian having the second set of values assigned to the embedding potentials.

While this specification contains many details, these should not be understood as limitations on the scope of what may be claimed, but rather as descriptions of features specific to particular examples. Certain features that are described in this specification or shown in the drawings in the context of separate implementations can also be combined. Conversely, various features that are described or shown in the context of a single implementation can also be implemented in multiple embodiments separately or in any suitable sub combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single product or packaged into multiple products.

A number of embodiments have been described. Nevertheless, it will be understood that various modifications can be made. Accordingly, other embodiments are within the scope of the following claims.

What is claimed is:

1. A quantum simulation method performed by a computer system comprising at least one classical processor unit and a plurality of unentangled quantum processor units (QPUs), wherein the at least one classical processor unit is communicably coupled to the plurality of unentangled QPUs by respective interfaces, the quantum simulation method comprising:
by operation of the at least one classical processor unit:
identifying fragments of a quantum system; and
generating a set of models representing the quantum system, the set of models comprising subsystem models representing the respective fragments of the quantum system; and
using the plurality of unentangled QPUs to execute the respective subsystem models in a simulation of the quantum system, wherein using the plurality of unentangled QPUs to execute the respective subsystem models comprises delegating sub-processes to the plurality of unentangled QPUs, and delegating the sub-processes comprises:
sending instructions from the at least one classical processor unit to the plurality of unentangled QPUs through the respective interfaces; and
receiving outputs from the plurality of unentangled QPUs through the respective interfaces.

2. The quantum simulation method of claim 1, wherein executing the subsystem models comprises using two or more of the unentangled QPUs to execute two or more of the subsystem models in parallel.

3. The quantum simulation method of claim 1, comprising simulating the quantum system by executing the set of models on the computer system, wherein simulating the quantum system comprises using density matrix embedding theory (DMET) to compute an approximate ground state energy for the quantum system.

4. The quantum simulation method of claim 3, wherein using the unentangled QPUs to execute the respective subsystem models comprises executing a variational quantum eigensolver (VQE) algorithm on each QPU to compute reduced density matrices (RDMs) for the respective fragments.

5. The quantum simulation method of claim 4, comprising computing the approximate ground state energy from the RDMs.

6. The quantum simulation method of claim 4, wherein the QPUs execute the VQE algorithm to compute two-particle reduced density matrices (2-RDMs) for the respective fragments.

7. The quantum simulation method of claim 4, wherein the set of models comprises an approximate Hamiltonian for the quantum system, the approximate Hamiltonian comprises embedding potentials associated with the respective fragments, the subsystem models comprise embedded Hamiltonians for the respective fragments, and the QPUs compute the RDMs based on the embedded Hamiltonians.

8. The quantum simulation method of claim 7, wherein simulating the quantum system comprises, by operation of the at least one classical processor unit:
computing an approximate ground state of the quantum system based on the approximate Hamiltonian having an initial set of values assigned to the embedding potentials; and
computing an updated set of values for the embedding potentials based on the RDMs computed by the QPUs.

9. The quantum simulation method of claim 7, wherein simulating the quantum system comprises executing an iterative process, and each iteration of the iterative process comprises:
computing an approximate ground state of the quantum system for the iteration based on the approximate Hamiltonian;
generating subsystem models for the iteration based on the approximate ground state for the iteration;
by operation of the unentangled QPUs, computing updated RDMs for the respective fragments based on the subsystem models for the iteration; and
computing an updated set of values for the embedding potentials based on the updated RDMs.

10. The quantum simulation method of claim 1, wherein at least one of the plurality of unentangled QPUs comprises a superconducting circuit comprising a plurality of qubit devices, each of the qubit devices comprising at least one Josephson junction.

11. The quantum simulation method of claim 1, wherein the set of models comprises a high-level quantum system model, the subsystem models are low-level quantum system models, and the method comprises:
using the at least one classical processor unit to execute the high-level quantum system model in the simulation of the quantum system; and
using the plurality of unentangled QPUs to execute the low-level quantum system models in the simulation of the quantum system.

12. The quantum simulation method of claim 1, comprising, by operation of the at least one classical processor unit, identifying the fragments and parameterizing the subsystem models for execution by the unentangled QPUs based on hardware and performance capabilities of the unentangled QPUs.

13. The quantum simulation method of claim 12, wherein each fragment represents a subspace within a Hilbert space defined by the quantum system, none of the fragments overlaps another fragment in the quantum system, and the fragments collectively constitute the entire quantum system.

14. The quantum simulation method of claim 1, comprising, by operation of the at least one classical processor unit, integrating the outputs from the plurality of unentangled QPUs in the simulation of the quantum system.

15. The quantum simulation method of claim 1, comprising, by operation of the at least one classical processor unit, delegating further sub-processes based on the outputs from the plurality of unentangled QPUs.

16. The quantum simulation method of claim 1, wherein at least a subset of the plurality of unentangled QPUs operate in disparate locations.

17. The quantum simulation method of claim 1, wherein at least one of the interfaces comprises a local area network, and delegating the sub-processes comprises:
sending instructions from the at least one classical processor unit to at least one of the plurality of unentangled QPUs through the local area network; and
receiving outputs from at least one of the plurality of unentangled QPUs through the local area network.

18. The quantum simulation method of claim 1, wherein at least one of the interfaces comprises the Internet, and delegating the sub-processes comprises:
sending instructions from the at least one classical processor unit to at least one of the plurality of unentangled QPUs through the Internet; and
receiving outputs from at least one of the plurality of unentangled QPUs through the Internet.

19. A computer system comprising:
a plurality of unentangled quantum processor units (QPUs);
interfaces communicably connected to the plurality of unentangled QPUs:
one or more classical processor units configured to perform operations comprising:
identifying fragments of a quantum system:
generating a set of models representing the quantum system, the set of models comprising subsystem models representing the respective fragments of the quantum system; and
using the unentangled QPUs to execute the respective subsystem models, wherein using the unentangled QPUs to execute the respective subsystem models comprises delegating sub-processes to the unentangled QPUs, and delegating the sub-processes comprises:
sending instructions from the one or more classical processor units to the plurality of unentangled QPUs through the respective interfaces: and
receiving outputs from the plurality of unentangled QPUs through the respective interfaces.

20. The computer system of claim 19, wherein using the unentangled QPUs comprises using two or more of the unentangled QPUs concurrently to execute two or more of the subsystem models in parallel.

21. The computer system of claim 19, wherein the one or more classical processor units are configured to use the unentangled QPUs to execute the subsystem models in a simulation that computes an approximate ground state energy for the quantum system.

22. The computer system of claim 21, wherein using the unentangled QPUs to execute the respective subsystem models comprises executing a variational quantum eigensolver (VQE) algorithm on each QPU to compute reduced density matrices (RDMs) for the respective fragments.

23. The computer system of claim 22, wherein the one or more classical processor units are configured to compute the approximate ground state energy from the RDMs.

24. The computer system of claim 22, wherein the QPUs are configured to execute the VQE algorithm to compute two-particle reduced density matrices (2-RDMs) for the respective fragments.

25. The computer system of claim 22, wherein the set of models comprises an approximate Hamiltonian for the quantum system, the approximate Hamiltonian comprises embedding potentials associated with the respective fragments, and the subsystem models comprise embedded Hamiltonians for the respective fragments.

26. The computer system of claim 25, wherein the one or more classical processor units are configured to perform operations comprising:
computing an approximate ground state of the quantum system based on the approximate Hamiltonian having an initial set of values assigned to the embedding potentials; and
computing an updated set of values for the embedding potentials based on the RDMs computed by the QPUs.

27. The computer system of claim 25, wherein the one or more classical processor units are configured to execute an iterative process, and each iteration of the iterative process comprises:
computing an approximate ground state of the quantum system for the iteration based on the approximate Hamiltonian;
generating subsystem models for the iteration based on the approximate ground state for the iteration;
by operation of the unentangled QPUs, computing updated RDMs for the respective fragments based on the subsystem models for the iteration; and
computing an updated set of values for the embedding potentials based on the updated RDMs.

28. The computer system of claim 19, wherein at least one of the plurality of unentangled QPUs comprises a superconducting circuit comprising a plurality of qubit devices, each of the qubit devices comprising at least one Josephson junction.

29. The computer system of claim 19, the operations comprising identifying the fragments and parameterizing the subsystem models for execution by the unentangled QPUs based on hardware and performance capabilities of the unentangled QPUs.

30. The computer system of claim 19, the operations comprising integrating the outputs from the plurality of unentangled QPUs in the simulation of the quantum system.

31. The computer system of claim 19, the operations comprising delegating further sub-processes based on the outputs from the plurality of unentangled QPUs.

32. The computer system of claim 19, wherein at least a subset of the plurality of unentangled QPUs reside in disparate locations.

33. The computer system of claim 19, wherein at least one of the interfaces comprises a local area network.

34. The computer system of claim 19, wherein at least one of the interfaces comprises the Internet.

* * * * *